(12) United States Patent
Warburton

(10) Patent No.: US 8,167,953 B2
(45) Date of Patent: May 1, 2012

(54) CARPOMETACARPAL (CMC) JOINT ARTHROPLASTY IMPLANTS AND RELATED JIGS, MEDICAL KITS AND METHODS

(75) Inventor: Mark J. Warburton, High Point, NC (US)

(73) Assignee: Piper Medical, Inc., High Point, NC (US)

( * ) Notice: Subject to any disclaimer, the term of this patent is extended or adjusted under 35 U.S.C. 154(b) by 0 days.

(21) Appl. No.: 13/005,882

(22) Filed: Jan. 13, 2011

(65) Prior Publication Data

US 2011/0106269 A1     May 5, 2011

Related U.S. Application Data

(63) Continuation of application No. 12/109,511, filed on Apr. 25, 2008, now abandoned.

(60) Provisional application No. 60/914,449, filed on Apr. 27, 2007.

(51) Int. Cl.
*A61F 2/42* (2006.01)
*A61F 5/00* (2006.01)
*A61F 2/46* (2006.01)

(52) U.S. Cl. ............ 623/21.16; 623/21.15; 606/87; 606/96; 606/86 R

(58) Field of Classification Search .... 623/21.11–21.19; 606/86–89, 96, 79, 82

See application file for complete search history.

(56) References Cited

U.S. PATENT DOCUMENTS

| | | | |
|---|---|---|---|
| 4,156,296 A | | 5/1979 | Johnson et al. |
| 5,308,412 A | | 5/1994 | Shetty et al. |
| 5,417,694 A | * | 5/1995 | Marik et al. ............ 606/88 |
| 5,702,469 A | | 12/1997 | Whipple et al. |
| H1706 H | * | 1/1998 | Mason ............................ 606/87 |
| 6,126,690 A | | 10/2000 | Ateshian et al. |
| 7,250,061 B2 | | 7/2007 | Jacobsson et al. |
| 7,371,240 B2 | * | 5/2008 | Pinczewski et al. ............ 606/88 |
| 2006/0111787 A1 | * | 5/2006 | Bailie et al. ................. 623/19.13 |
| 2006/0247787 A1 | | 11/2006 | Rydell et al. |
| 2009/0088758 A1 | * | 4/2009 | Bennett ........................... 606/82 |

OTHER PUBLICATIONS

Ascension Orthopedics, prohemisphere, www.ascensionortho.com, product advertisement, 1 page, date unknown, but for examination purposes, is before Apr. 2007.

Ascension Orthopedics, saddle cmc, www.ascensionortho.com, product advertisement, 1 page, date unknown, but for examination purposes, is before Apr. 2007.

Badia et al., *Total Joint Arthroplasty in the Treatment of Advanced Stages of Thumb Carpometacarpal Joint Osteoarthritis*, The Journal of Hand Surgery, vol. 31A No. 10, pp. 1605-1614 and 1605.e12, Dec. 2006.

BioPro Modular Thumb Implant, www.bioproimplants.com, product advertisement, 1 page, date unknown, but for examination purposes, is before Apr. 2007.

Small Bone Innovations, Artelon CMC Spacer, www.totalsmallbone.com, product advertisement, 2 pages (©2006).

(Continued)

*Primary Examiner* — David Isabella
*Assistant Examiner* — Marcia Hoffman
(74) *Attorney, Agent, or Firm* — Myers Bigel Sibley & Sajovec, P.A.

(57) ABSTRACT

Thumb carpometacarpal (CMC) joint implants include a trapezium implant defining an articulating surface and a cooperating first metacarpal implant with a base portion of the first metacarpal defining an articulating surface. The first metacarpal base articulating-surface is configured to articulate against the trapezium implant articulating surface.

7 Claims, 27 Drawing Sheets

OTHER PUBLICATIONS

The Journal of Hand Surgery, Appendix 2 and 3, vol. 31A No. 10, Dec. 2006, 1 page (1605.e12).
Wright Medical Technology, Inc., Tie-in Trapezium Implant, www.wmt.com, product advertisement, 2 pages (©2004).
Wright Medical Technology, Inc., Swanson Basal Thumb Implant, product advertisement, 1 page, date unknown, but for examination purposes, is before Apr. 2007.
Wright Medical Technology, Inc., Orthoshere, product advertisement, 1 page, date unknown, but for examination purposes, is before Apr. 2007.
Zancolli et al., Biomechanics of the trapezio-metacarpal joint, Clinical Orthopaedics and Related Research, Jul. 1987, pp. 14-26, No. 220.

* cited by examiner

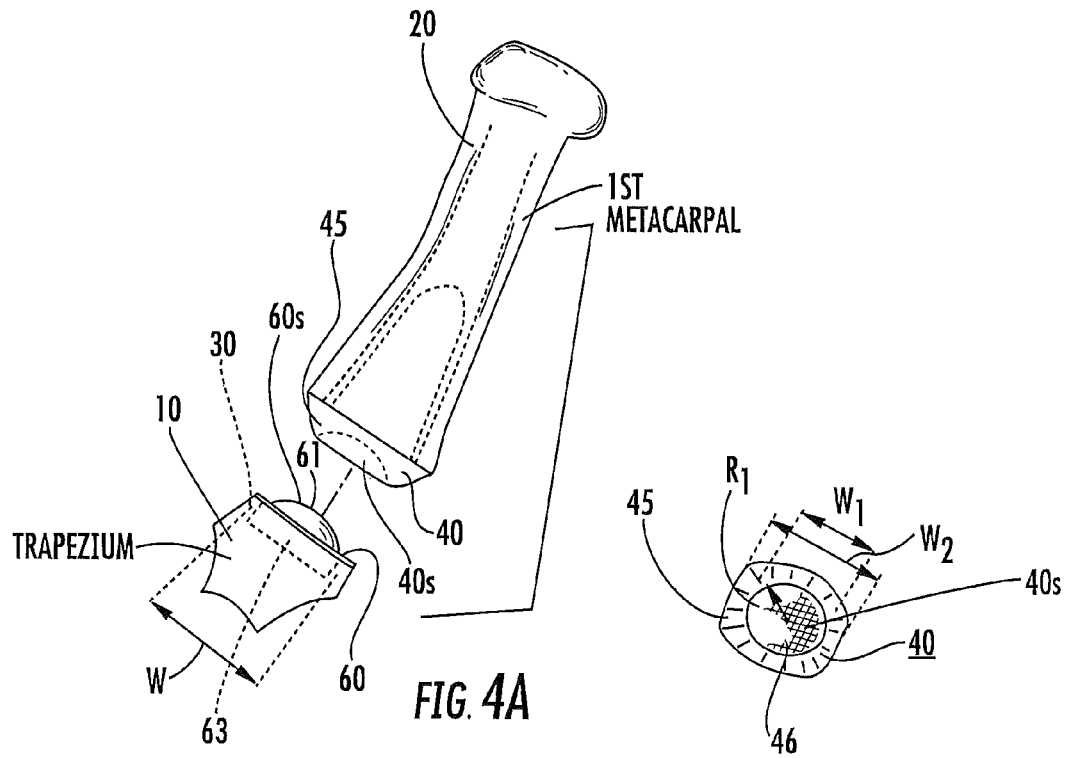
FIG. 4A
FIG. 4B
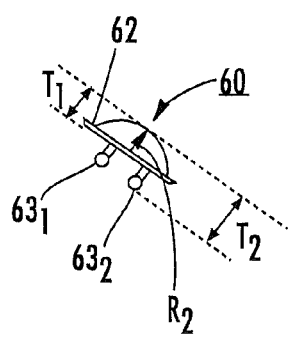
FIG. 4C
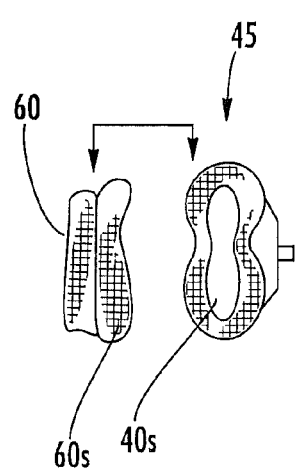
FIG. 4D

TRAPEZIUM TRIALS

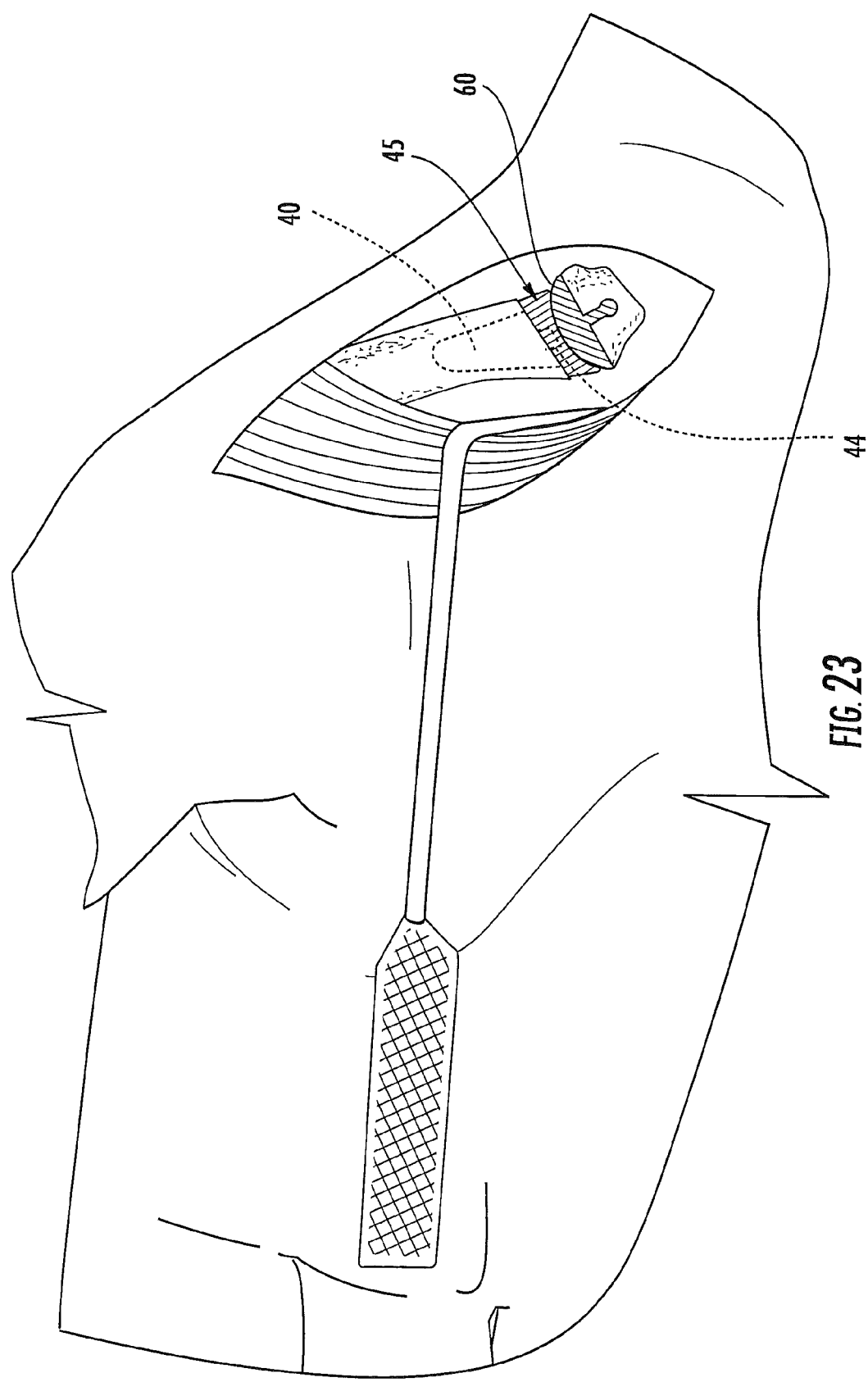

CARPOMETACARPAL (CMC) JOINT ARTHROPLASTY IMPLANTS AND RELATED JIGS, MEDICAL KITS AND METHODS

RELATED APPLICATIONS

This application is a continuation of U.S. patent application Ser. No. 12/109,511, filed Apr. 25, 2008 now abandoned, which claims the benefit of priority of U.S. Provisional Application Ser. No. 60/914,449 filed Apr. 27, 2007, the contents of which are hereby incorporated by reference as if recited in full herein.

FIELD OF THE INVENTION

This invention relates to implants suitable for use in treating pain and/or injury of the carpometacarpal joint.

BACKGROUND OF THE INVENTION

Basilar thumb arthritis (arthritis at the base of the thumb) of the carpo-metacarpal (CMC) joint is thought to be the most common arthritis of the homosapien. It typically presents as a symptomatic problem in the sixth decade of life and its incidence increases thereafter. It is a result of the rather recent phylogenetic appearance of a highly mobile, strong thumb ray. The thumb acts as the pivotal and guiding member of the defining anatomical features of the human, the prehensile hand. The brain's cortical representation area of the thumb is huge. The thumb allows for a panoply of activities from watch making to weightlifting. Unfortunately, this distinct anatomical advantage can result in arthritis of the CMC joint of the thumb.

It is believed that gaming and cell phone text-messaging and the like may also lead to basilar thumb arthritis, with a resulting increase in incidence as well as a potential earlier onset that has been conventional.

Anatomically, the CMC joint includes the trapezium articulating with the base of the first metacarpal as shown in FIG. 1. As shown in FIG. 2, the CMC joint is a saddle joint allowing abduction toward the palm, abduction away from the palm, opposition (toward the $5^{th}$ finger), and extension or retroposition (backward or hitch-hiker position.) As shown in FIG. 3B, the articular surface of the base of the $1^{st}$ metacarpal 20 is divided into dorsal and palmer slopes and a central saddle portion. As shown in FIG. 3A, the opposing articular surface of the trapezium 10 also has two parts: a spherical portion 11, which articulates with the slopes of the first metacarpal; and a saddle portion 12, which articulates with the saddle portion of the $1^{st}$ metacarpal. (See, e.g., Zancolli et al., *Biomechanics of the trapezio-metacarpal joint*, Clinical Orthopaedics and Related Research, No. 220, July 1987, pp. 14-26). FIG. 3C illustrates an enlarged "normal" or "natural" trapezium 10 and first metacarpal base 20b.

The subchondral (below cartilage) bone of the trapezium-first metacarpal is covered by hyaline cartilage. This cartilage is typically the first tissue to deteriorate during arthritic wear of the joint. Initially, thinning and pitting occurs, which can be followed by osteophyte (bone spur) formation and subluxation (loss of congruity) of the joint.

Over the past fifty years various arthroplasties have been proposed to try to alleviate the disabling pain of CMC arthritis. Generally stated, the arthroplasties have been either soft tissue interpositions, implant interpositions, or partial joint replacements using implants. The implant procedures either have replaced the base of the first metacarpal or replaced the trapezium following trapezectomy.

Currently, $1^{st}$ metacarpal implants involve inserting an intramedullary stem into the base of the $1^{st}$ metacarpal, to which is attached a convex articular surface replacement. Trapezial implants generally have the shape of the anatomic trapezium. In both cases, an implant material (e.g., metal, silicone, or ceramic) articulates with a bone surface where motion occurs. These procedures do not attempt to replace the joint but rather act as spacers. Fortunately, they can reduce the arthritic pain, but problems have arisen. Potential problems include implant loosening, implant breakage, implant dislocation, adverse tissue reaction to the implant (particularly silicone), failure of pain relief, loss of strength, and implant subsidence (sinking in or erosion of the residual trapezium, as in $1^{st}$ metacarpal implants). It is believed that because of these problems, the most common procedure currently performed for CMC arthritis is a soft tissue interposition suspension procedure also known as "ligament reconstruction with tendon interposition (LRTI)" where no implant is used.

In view of the foregoing, there remains a need for alternative thumb CMC implants.

SUMMARY OF EMBODIMENTS OF THE INVENTION

In some embodiments, thumb CMC joint implants include a trapezium implant defining an articulating surface and a cooperating first metacarpal implant with a base portion of the first metacarpal defining an articulating surface. The first metacarpal base articulating-surface is configured to articulate against the trapezium implant articulating surface.

Embodiments of the present invention can replace both the base of the first metacarpal and the opposing articular surface of the trapezium, resulting in a total thumb CMC arthroplasty (TCMA).

In some embodiments, the trapezium implant includes at least one downwardly extending anchoring member. The at least one anchoring member can include a plurality of transversely spaced apart keels extending at least a major portion of a length or width dimension of the trapezium implant.

In some embodiments, the trapezium implant can include a projecting portion that forms the articular surface. The first metacarpal base portion can include a recessed cavity that matably receives the projecting portion of the trapezium implant, thereby allowing articulating motion between the trapezium implant and the first metacarpal base.

The trapezium implant can have a projecting portion that extends outside the bounds of the trapezium into the CMC cavity to define a substantially convex articular surface. The first metacarpal implant base portion can have a socket with a substantially concave cavity sized and configured to matably receive the projecting portion of the trapezium implant.

Other embodiments are directed to medical kits for thumb CMC joint arthoplasty. The kits include: (a) at least one trapezium implant; (b) at least one first metacarpal intramedullary stem implant; and (c) a plurality of base members having different sizes and/or shapes, each of the base members configured to serially attach to the first metacarpal intramedullary stem implant. In position, the attached base member of the intramedullary implant and the trapezium implant articulate against each other.

In some embodiments, the at least one trapezium implant includes at least one downwardly extending anchoring member configured to reside in local bone of a target trapezium.

The medical kits can also include a plurality of trial trapezium implants. The trials have a substantially planar bottom surface and can have a non-binding fin or keel or are devoid of a downwardly extending anchoring member.

The medical kits may also include at least one trapezium implant jig configured to define a bone preparation guide or template for preparing a target trapezium to accept the trapezium implant.

Still other embodiments are directed to jigs for a thumb CMC arthoplasty procedure. The jigs include a rigid body having a substantially planar top segment that merges into a substantially planar downwardly extending side segment and at least one slot extending across at least a portion of the top segment and down into at least a portion of the side segment. The slot is sized and configured to define a cutting guide for a target trapezium.

In particular embodiments, the slot is substantially straight and substantially horizontal across the top segment and substantially vertical along the side segment.

Other embodiments are directed to methods for treating and/or repairing a CMC joint in a patient. The methods include: (a) implanting a trapezium implant in a target trapezium so that the trapezium implant defines an articulating surface; and (b) implanting a first metacarpal implant into the first metacarpal so that the first metacarpal implant defines an articulating surface that articulates against the trapezium implant articulating surface.

In some embodiments, the methods also include, before the step of implanting the trapezium implant: (i) preparing the target trapezium for receiving the trapezium implant by planarizing the natural articular surface of the target trapezium, then forming a channel in the target trapezium; and (ii) trying different size trapezium trials to determine a proper size trapezium implant for the patient.

The methods may also include, before the step of implanting the trapezium implant, temporarily affixing a jig with a drilling and cutting channel guide to the trapezium, and drilling and cutting a channel into the target using the jig drilling and cutting channel guide.

In some embodiments, the first metacarpal implant comprises an elongate intramedullary stem and an attachable base member with a socket, and the method further includes, before the step of implanting the first metacarpal implant, trying different size base members to select a base member that substantially fills the CMC cavity.

The foregoing and other objects and aspects of the present invention are explained in detail in the specification set forth below.

BRIEF DESCRIPTION OF THE DRAWINGS

FIG. 4A is a side perspective view of a 1st metacarpal implant with a cooperating trapezium implant according to embodiments of the present invention.

FIG. 4B is an end view of the 1st metacarpal implant shown in FIG. 4A.

FIG. 4C is an exemplary end view of the trapezium implant shown in FIG. 4A according to some embodiment of the present invention.

FIG. 4D is a top perspective view of an alternate configuration of the distal end member (the shape being similar to the natural articular surface of the CMC joint) according to some embodiments of the invention.

FIGS. 16-23 illustrate exemplary steps that can be used to surgically implant a total TCMA prosthesis according to embodiments of the present invention.

DESCRIPTION OF EMBODIMENTS OF THE INVENTION

Figure 1:
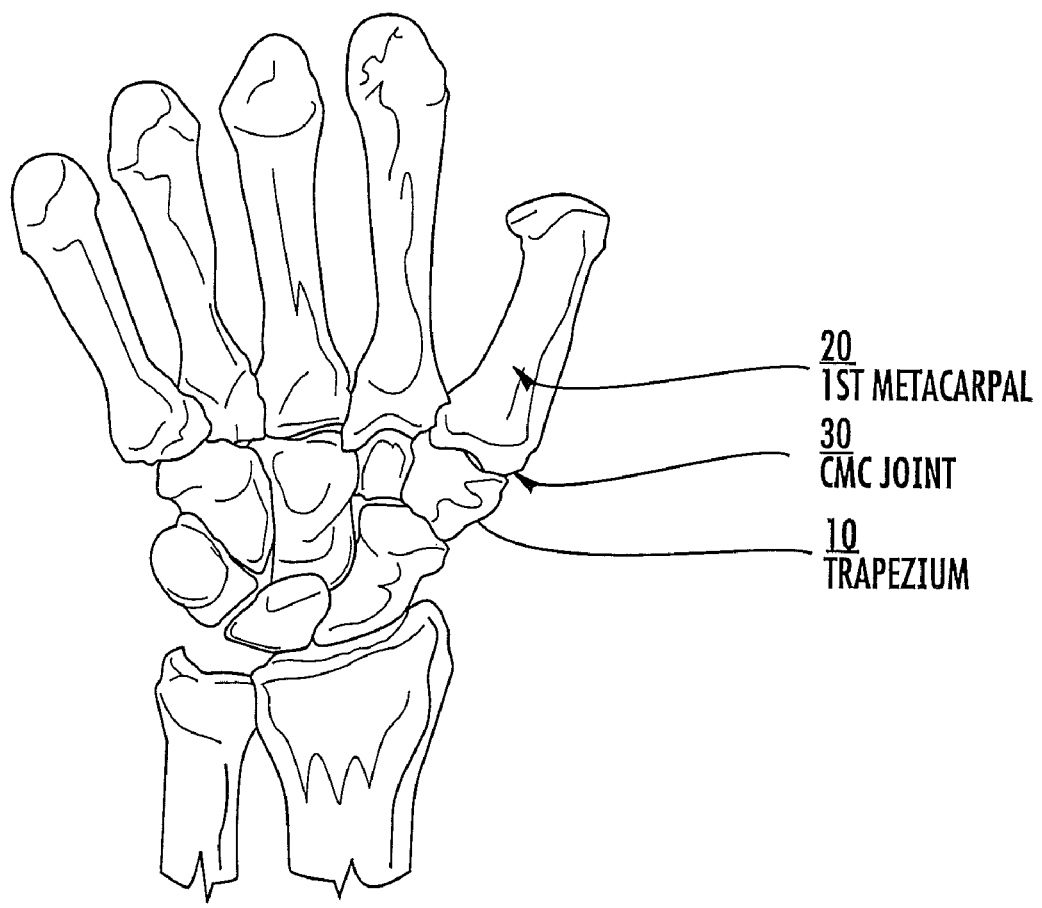
FIG. 1 is an anatomical drawing of the palmar aspect of the carpal and metacarpal bones illustrating the 1st metacarpal, the CMC joint and the trapezium.
Figure 2:
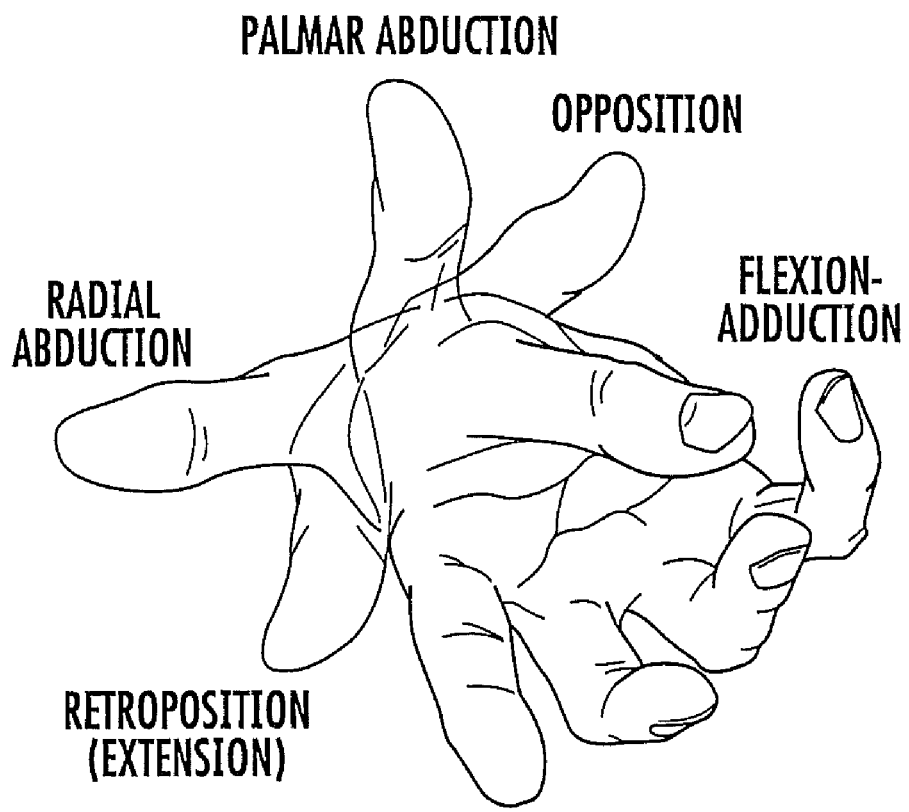
FIG. 2 is an axial view illustrating motions of the thumb.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein. The term "polymer" includes copolymers and derivatives and/or combinations thereof.

The implant can be a total joint replacement implant that allows articulation of the bones. The term "total joint replacement" means that both the base of the first metacarpal and the opposing articular surface of the trapezium are replaced with cooperating implant surfaces, resulting in a total thumb carpo-metacarpal arthroplasty (TCMA), thereby providing complete joint replacement as in total hip arthroplasty (THA) or total knee arthroplasty (TKA).

As shown in FIG. 4A, embodiments of the invention provide an intramedullary first metacarpal implant 40 that cooperates with a trapezium implant 60. The first metacarpal implant 40 includes a base portion 45 that defines a base of the CMC joint. As shown, the base portion 45 has a socket 46 (FIG. 4B) that matably receives the projecting portion 61 of the trapezium implant 60, allowing articulation between the two implants 40, 60 such that the corresponding articulating surfaces 40s, 60s articulate against each other. In the embodiment shown in FIG. 4A, the first metacarpal implant 40 has a substantially concave articulating surface 40s substantially matched to a convex articulating surface 60s of the trapezium implant 60. The first metacarpal implant 40 can be a single unitary member or can include a matable base member that defines the articulating surface 40s. For example, if the implants 40, 60 comprise pyrocarbon or a similarly lubricious and/or strong composite or polymer, the two surfaces 40s, 60s can articulate against each other without requiring an intermediary material or component. Alternatively, if the first metacarpal implant 40 and trapezium implant 60 are made out of stainless steel or titanium or other suitable biomedical metal, then a base member (typically attached to the first implant 40) can be used to define one of the articulating surfaces, formed of a suitable biocompatible material, such as, for example, polyethylene (so that there is no "metal on metal" contact for the articulating surfaces 40s, 60s).

Figure 3A:
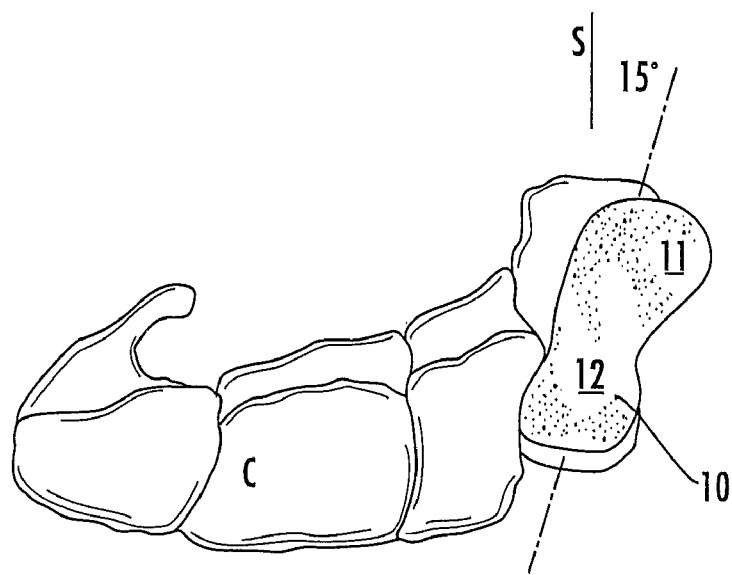
FIGS. 3A and 3B are schematic illustrations of the bones of the trapezio-metacarpal joint (the upper bones associated with the trapezium and the lower bones associated with the metacarpal).
Figure 3B:
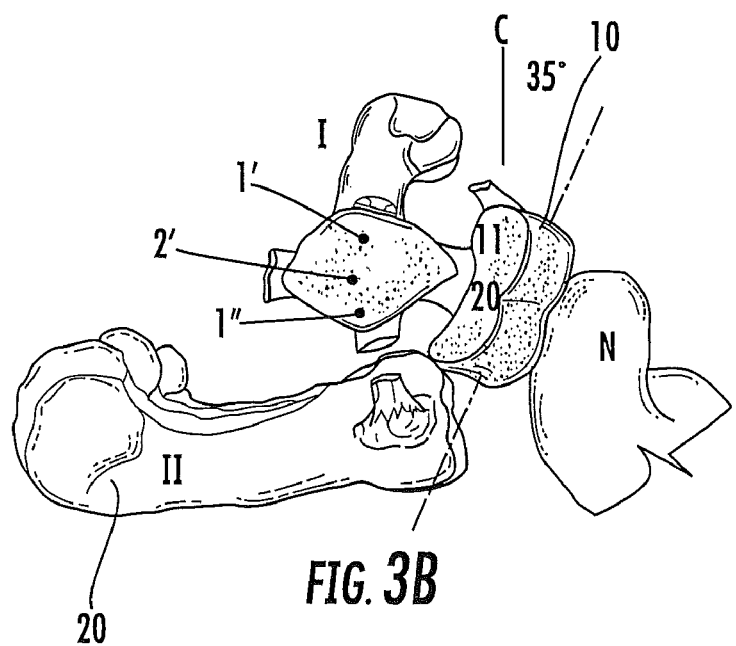
Figure 3C:
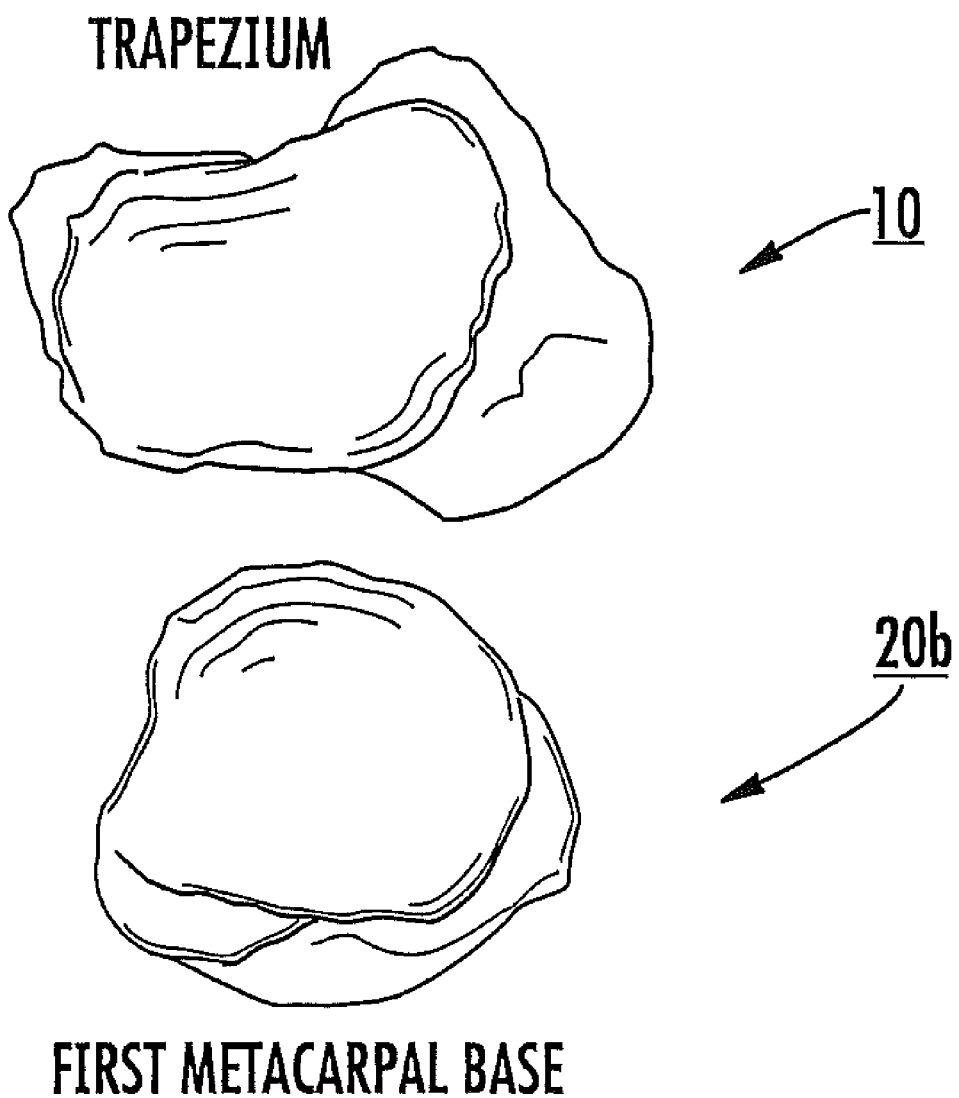
FIG. 3C is an enlarged schematic illustration of the corresponding articular surfaces of the metacarpophalangeal joint (the trapezium and the first metacarpal base).

In other embodiments, the first metacarpal implant 40 can include a base portion 45 that is shaped as a substantially anatomically equivalent of a natural metacarpal base (FIGS. 3B and 3C) and, similarly, the trapezium implant 60 can have a corresponding substantially natural anatomic distal articular surface that can cooperate with the first metacarpal implant 40. Examples of implants 45, 60 with alternative articulating surfaces 40s, 60s having more natural surface contours are shown in FIG. 4D. The implants 40, 60 can thus define a natural anatomical contour of the CMC joint to act as a resurfacing implant system.

FIG. 4B is an end view of the base portion 45 of the first metacarpal implant 40 shown in FIG. 4A that can define a receiving socket 46 with the articulating surface 40s forming part of the CMC replacement joint. The socket 46 can have a width "$W_1$" with an overall width of the base portion 45 can have a width "$W_2$". The implant 40 can be provided in different sizes with different widths, recognizing that the anatomical constraints and needs will likely vary by patient (age, gender, bone structure and the like). In some embodiments, the socket 46 has a concave hemispherical shape with an arc radius $R_1$.

FIG. 4C illustrates an end view of the trapezium implant 60 shown in FIG. 4A. As shown, the implant 60 includes at least one anchoring member 63, shown as two keels $63_1$, $63_2$. More or fewer anchoring members 63 can be used and different anchoring member configurations may also be used. FIG. 4A illustrates that the anchoring member 63 can be oriented to extend transversely across at least a major portion of the width of the implant 60.

The keels $63_1$, $63_2$ are typically rigid and reside in a bone tunnel or channel formed in the trapezium, but may be flexible and/or otherwise configured to promote and/or allow for local tissue ingrowth. The implant 60 can have a substantially planar bottom mounting surface 62 and the at least one anchoring member 63 can extend below the bottom surface 62. As shown, the anchoring member 63 can extend downwardly substantially orthogonal to the mounting surface 62, but the anchoring member 63 may be oriented at different angles.

The thickness $T_1$ of the projecting portion of the trapezium implant 60 can vary to allow a clinician to select the size that substantially fills the target CMC cavity. Sets of the implant 60 can be provided with different thickness $T_1$ to allow a clinician to select an appropriate one for the patient, as, again, the desired thickness may vary dice to target anatomical considerations, age, gender and the like. The downwardly extending length of the anchoring member 63 (e.g., keels $63_1$, $63_2$), is typically between about 0.1 inch to about 0.25 inches, defining an overall thickness $T_2$. In some embodiments, the projecting portion (e.g., dome) 61 can have a convexity with a radius $R_2$ that may, in some particular embodiments, be between about ⅛ inch to about ⅜ inches, which is typically slightly less than that of the socket radius $R_1$, thereby allowing for an articulating snug fit to inhibit misalignment or separation during articulation.

Figure 5A:
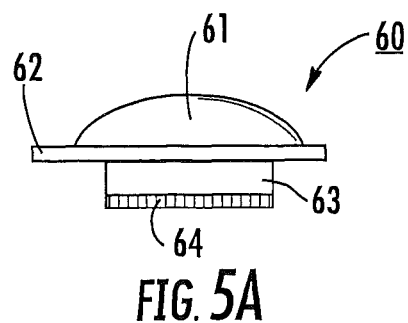
FIG. 5A is an enlarged side view of the trapezium implant shown in FIG. 4A.
Figure 5B:
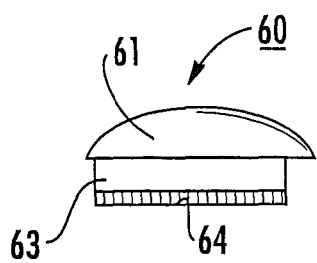
FIG. 5B is an enlarged side view of an alternate configuration of the trapezium implant shown in FIG. 4A.
Figure 5C:
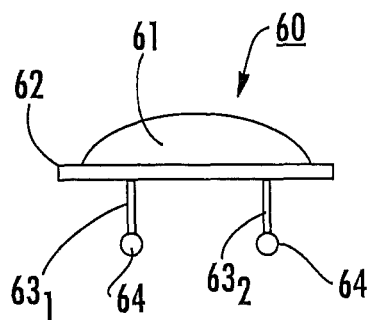
FIG. 5C is an enlarged end view of the trapezium implant shown in FIG. 5A or 5B.
Figure 5D:
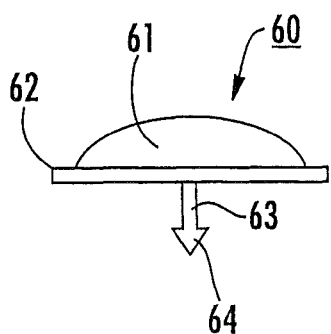
FIG. 5D is an enlarged end view of an alternative configuration of the trapezium implant shown in FIG. 5A or 5B according to some embodiments of the invention.

FIG. 5A is an enlarged side view of the trapezium implant 60. As shown, the at least one anchoring member 63 can reside inside the bounds of the bottom surface 62 and terminate prior to the outer portions thereof. FIG. 5B illustrates that the at least one anchoring member 63 can extend closer to one outer side edge of the implant than the opposing side edge. FIG. 5C illustrates that the at least one anchoring member 63 can have a larger and/or differently configured lower portion 64. As shown, the at least one anchoring member 63 can have a substantially thin planar body that merges into a substantially circular (cross-section) lower portion 64. As will be discussed further below, the lower portion can reside in a correspondingly shaped tunnel or channel in local bone to help retain the implant in a desired position. Alternatively, or in combination with the anchoring member(s) 63, bone cement or other anchoring mechanisms may be used. FIG. 5D illustrates an alternative anchoring member configuration, located substantially medially on the implant body 60. The lower portion 64 may be flexible and able to be press fit into a holding bone channel or tunnel. Combinations of the above anchoring configurations or other configurations may also be used.

Figure 6:
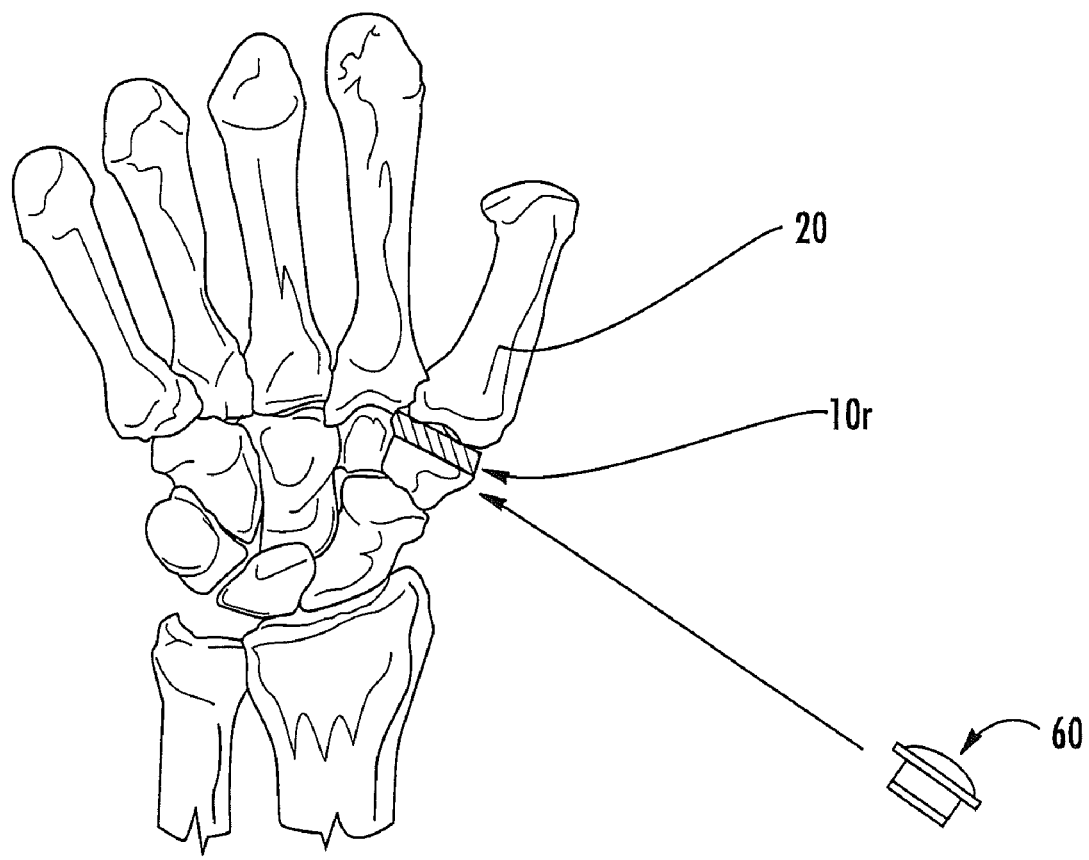
FIG. 6 is a schematic illustration of a thumb with a region of the trapezium removed to define a prepared distal surface suitable for the trapezium implant according to embodiments of the present invention.
Figure 7A:
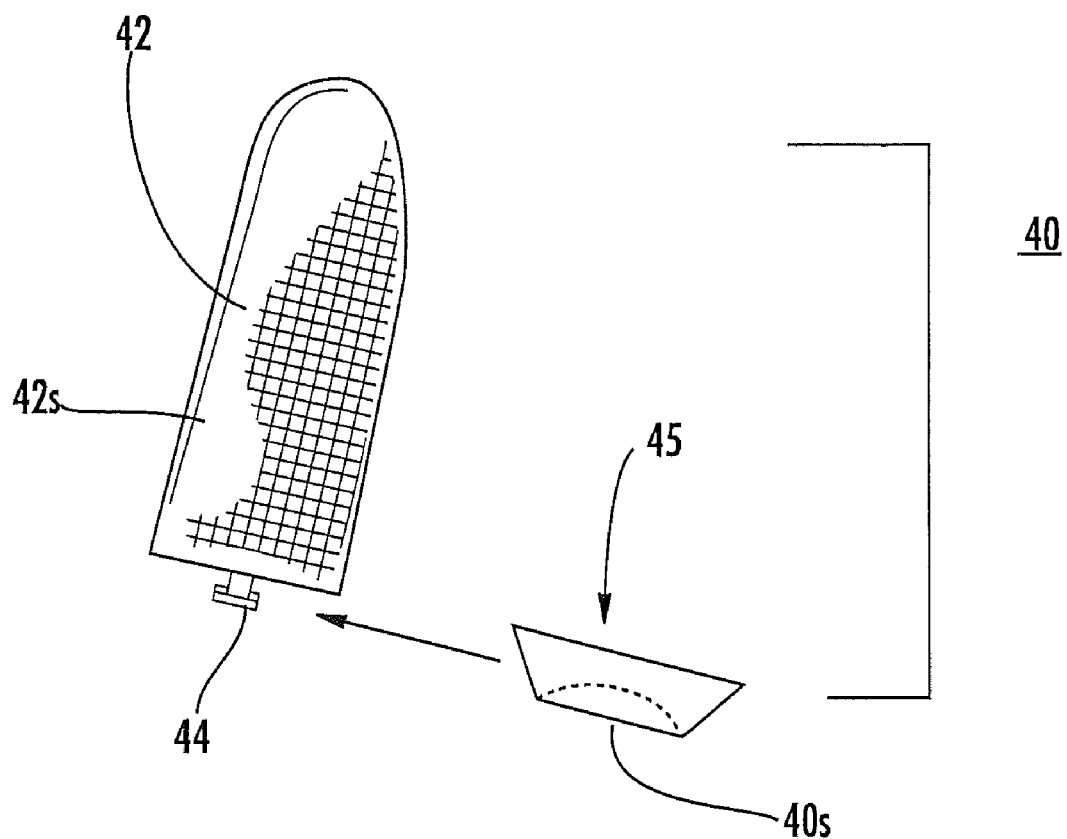
FIG. 7A is a side view of an intramedullary implant portion of a 1st metacarpal implant configured to matably attach to a selected distal end member (facing the trapezium).

To prepare the surgical site for the implants 40, 60, the base of the $1^{st}$ metacarpal can be planarized and/or flattened and the intramedullary implant 42 can be inserted into the proximal portion of the $1^{st}$ metacarpal 20. Similarly, as shown in FIG. 6, the distal articulating portion 10r of the anatomic trapezium can be removed to flatten and planarize the implant support surface and the implant 60 can be attached to the remaining trapezium. The first metacarpal intramedullary component 42 can be selected to fill and match the contour of the target endosteal (inside) surface of the proximal aspect of the first metacarpal 20. FIG. 7A illustrates that the implant 40 can include a base portion 45 that is matably attachable to the intramedullary portion 42 (e.g., stem). The intramedullary portion 42 of the implant 40 can be provided in various sizes to allow for correct patient sizing. Similarly, the base portion 45 can be provided in different sizes and/or configurations to allow a clinician to select the appropriate size for a patient.

In some embodiments, the implants 40, 60 can be provided in S, M, L and XL sizes, such as in the exemplary sizes provided below. The size of the trapezium implant 60 will determine the desired size of the first metacarpal implant 40, making the size of the trapezium implant 60 determinate thereof.

| Size | Trapezium Radius | 1st MC base member |
|---|---|---|
| Small | 3-4 mm (typically about ⅛ inch (3.18 mm)) | matching |
| Medium | 5-7 mm (typically about ¼ inch (6.35 mm)) | matching |
| Large | 8-10 mm (typically about ⅜ inch (9.52 mm)) | matching |

Figure 7B:
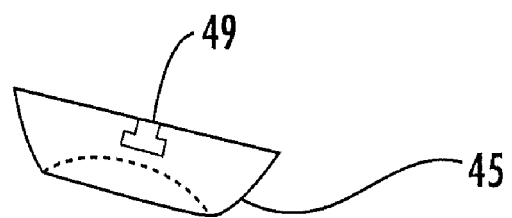
FIG. 7B is an opposing side view of the distal end member shown in FIG. 7A.
Figure 7C:
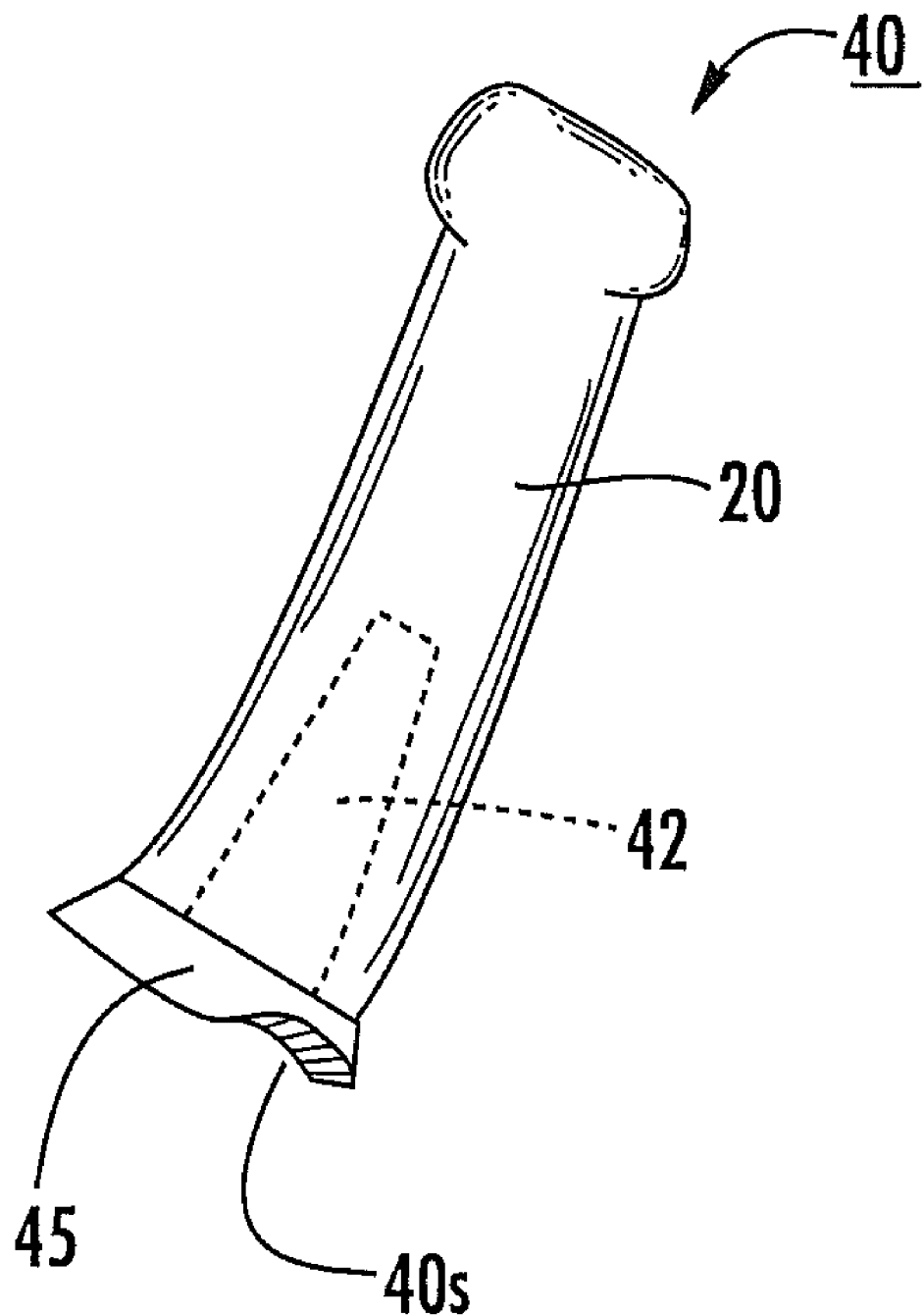
FIG. 7C is a side view of an articulating base member for a saddle configuration of the 1st metacarpal with the intramedullary portion of the implant in position and the distal end member attached thereto and extending beyond the bounds of the metacarpal to define an articular surface according to some embodiments of the present invention.
Figure 7D:
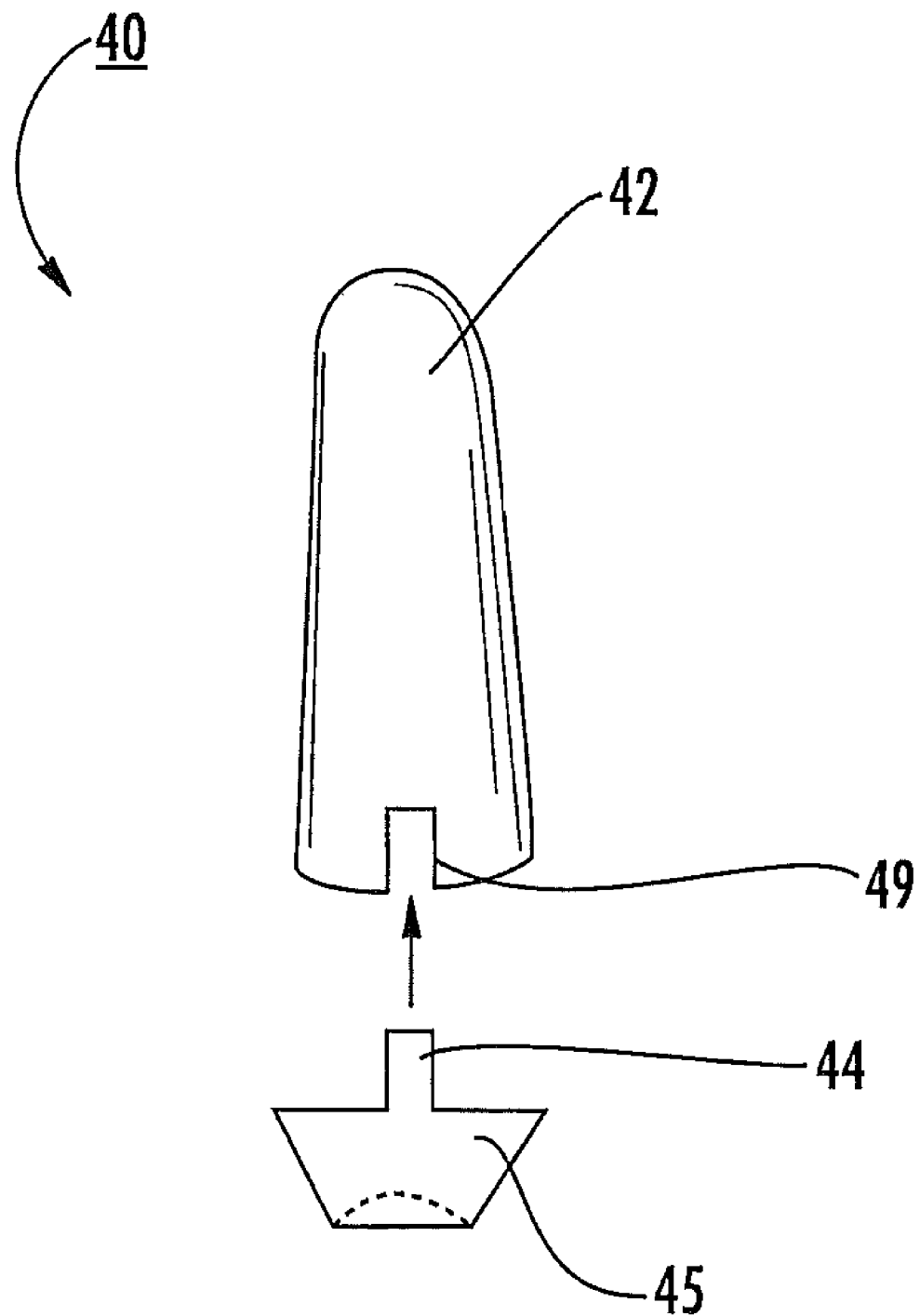
FIG. 7D is a side view of an alternate attachment configuration for the intramedullary member and the distal end member according to other embodiments of the invention.

The intramedullary surface 42s of the implant 42 can be roughened (cintered, pitted, scraped, filed, contoured, etc.) to promote bone ingrowth. The intramedullary implant 42 can be press fit into position, but also or alternatively can be cemented in with suitable biocompatible cement, such as, for example, polymethylmerthacolate. The intramedullary implant 42 can be manufactured out of various substantially rigid biocompatible materials, such as metals, rigidized polymers, ceramics, and/or carbon. As shown in FIG. 7A, the intramedullary implant 42 can include a locking member 44 to mate to the base portion 45 which defines the articular component. FIG. 7A shows that the locking member 44 can be a trunnion or post and FIG. 7B illustrates that the base portion 45 can include an aperture or channel 49 sized and configured to matably receive the locking member 44. FIG. 7C illustrates that the base portion 45 with the $1^{st}$ MC articulating component can have a saddle ("natural") configuration and may be snap-fitted and/or locked onto the proximal portion of the $1^{st}$ MC intramedullary component 42. FIG. 7D illustrates that the base portion 45 can include the locking member 44 while the intramedullary implant 42 can include the corresponding locking aperture 49. In other embodiments, the first metacarpal implant 40 can be pre-formed at an OEM or offsite location or defined by a single member (not shown).

In some embodiments, the intramedullary implant 42 and the trapezium implant 60 are metallic while the base portion 45 can comprise a polymer that provides the articulating surface 40s with the desired sliding frictional and/or lubricity property. The base portion 45 can be formed of a unitary member and material, similar to a spacer. In some embodiments, the base portion 45 comprises polyethylene. It can be provided in varying thicknesses as discussed herein in order to substantially fill the articulating cavity of the CMC joint. As also noted above, the articulating surface 40s can be substantially concave in shape but also can be fashioned more like an anatomic $1^{st}$ MC articular surface (e.g., saddle shaped), as noted above (see, e.g., FIGS. 4D, 7C).

The trapezial implant 60 has an articulating surface 60s that can be generally and/or substantially convex but also can be saddle shaped. The convex shape can reduce the stresses on the component at the bone implant interface.

Figure 8:
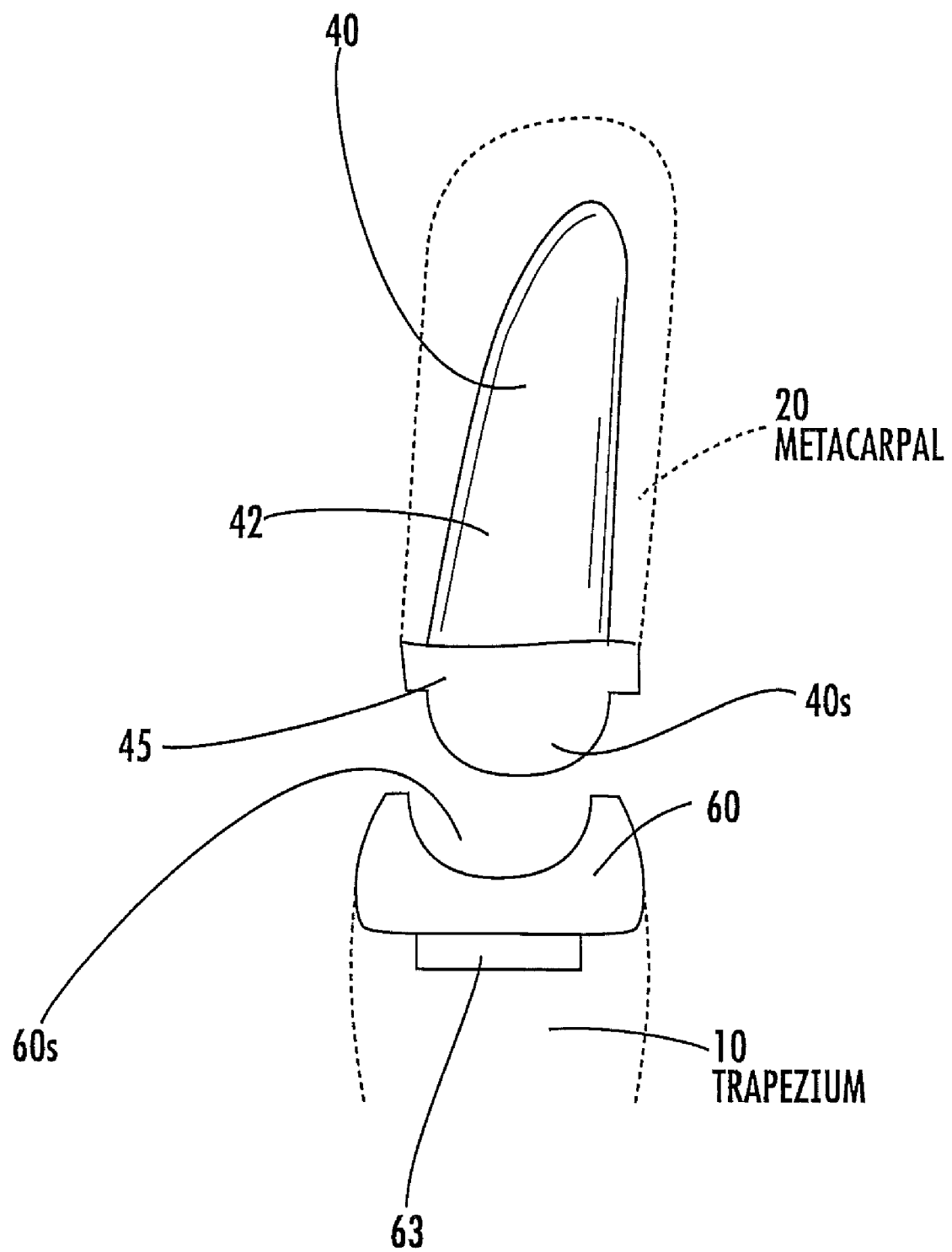
FIG. 8 is an exploded view of an alternate configuration of the trapezium implant and the cooperating 1st metacarpal implant according to yet other embodiments of the invention.

FIG. 8 also shows that the trapezium implant 60 can define a socket that has a substantially concave articulating surface 60s while the base portion 45 of the first metacarpal implant 40 can be substantially convex. The concave shape may reduce the stresses on the component at the bone implant interface.

The anchoring member 63 of the trapezium implant 60 can be configured to be resistance-fitted. The keel(s) and/or anchoring portion of the implant 60 can be forced into position by hammering, pushing and/or forcibly sliding the implant 60 into place. The placement can be done by overcoming the friction of the trapezial bone against the implant 60. A jig or series of jigs can be employed to prepare the implant bone site to facilitate the implantation (see, for example, an exemplary surgical procedure described below). The lower bone contact surface of the implant 60 and/or anchoring member(s) 63 can be roughened to promote bone ingrowth. The trapezium implant 60 can be configured to withstand loosening forces. The implant system can allow early motion, obviating the need for a cast post-operatively.

Surgical Procedure

It is contemplated that the implantation procedure should be able to be completed in less than about 1.5 hours. It may be performed under intravenous block anesthesia, but axillary block or general anesthesia are additional options. During the surgical procedure, the hand is typically in the palm up or semi-supinated position. A Wagner approach can be used, taking down the thenar muscles to expose the CMC capsule. A suitable needle, such as an 18-gauge needle, can be inserted into the CMC joint, identifying the joint. The CMC capsule can be incised axially, in line with the joint surface, taking care to preserve the capsular attachments to the trapezium and the base of the first metacarpal. The capsular cut can be made closer to the trapezium since the capsular attachment to the base of the $1^{st}$ MC is tenuous. As shown in FIG. 6, a wafer of bone comprising the articular surface is cut from the distal aspect of the trapezium with a suitable cutting member, such as, for example, a microsagital saw. This cut can be flat and made parallel to the scapho-trapezial joint, that is, perpendicular to the long axis of the trapezium. A thin wafer of articular surface can also be cut from the proximal aspect of the base of the first metacarpal (1$^{st}$ MC).

Figure 9A:
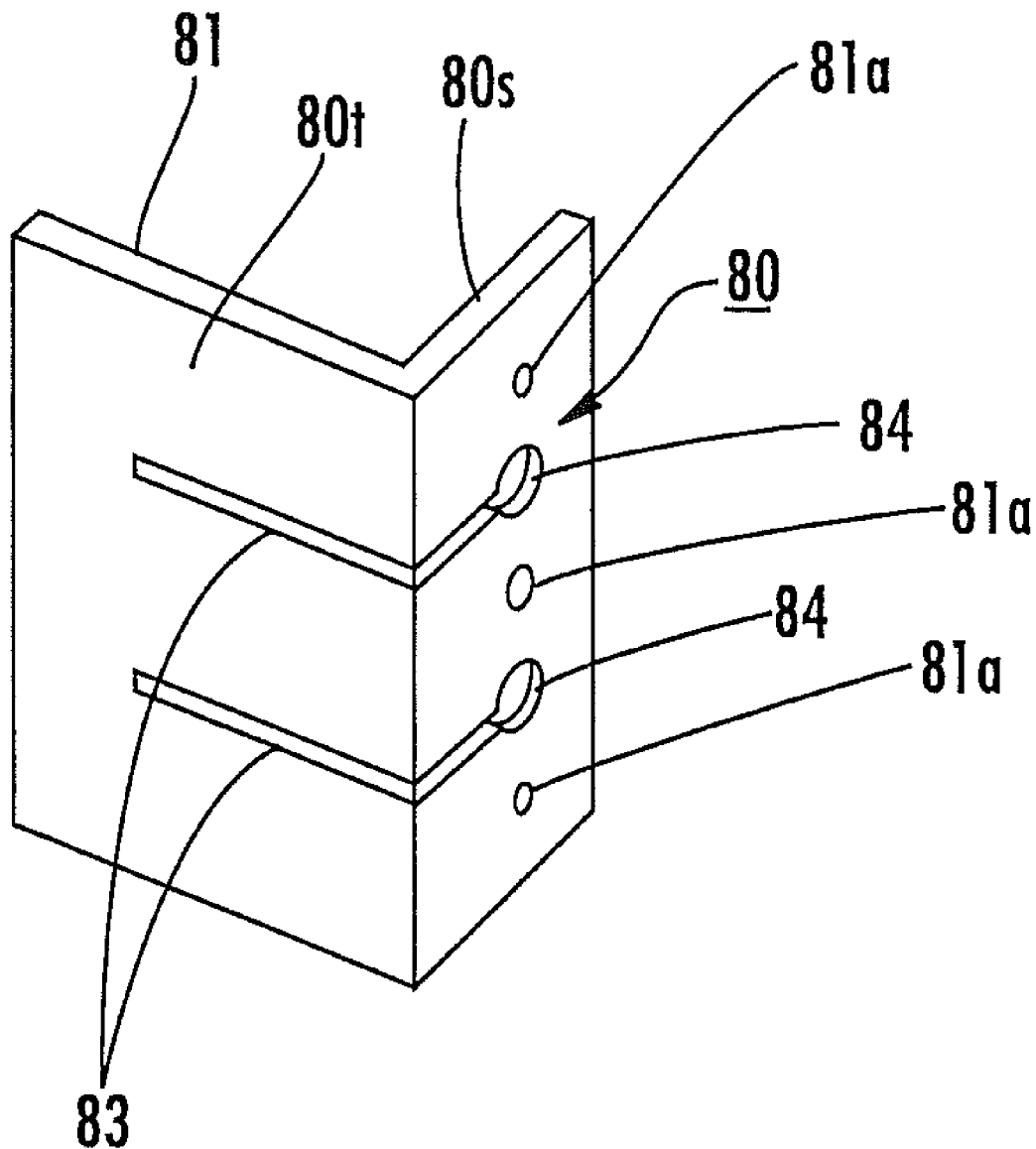
FIGS. 9A and 9B are schematic illustrations of a trapezial jig according to embodiments of the invention.

Next, as shown in FIG. 9A, a trapezial jig 80 is applied to the trapezium 10 with its flat top surface 81 placed against the distal cut surface of the trapezium. The jig 80 can be rigid and may be metallic. The jig 80 has a top segment 80s that merges into a downwardly-extending side segment 80s. The jig 80 can include cutting and drilling guide channels 83 and holding apertures 81a that allow pins, staples, nails, screws, wires and/or sutures to hold the jig 80 in position. The drilling and cutting guide channels 83 can be slots that extend across the top segment 80s down through at least a major portion of the side segment 80s. Although shown with two channels 83, the jig 80 can include one channel or more than two channels, typically corresponding to the number of anchoring members 63 (FIG. 5C). Also as shown, the channels 83 can end at a keyhole 84 that is sized and configured to correspond to a shape that can receive the lower portion of the anchoring member 63. As shown, the shape is circular, and may be sized to be the same or slightly less than the size of the lower portion of the anchoring member 64 for frictional fit thereof.

Figure 9B:
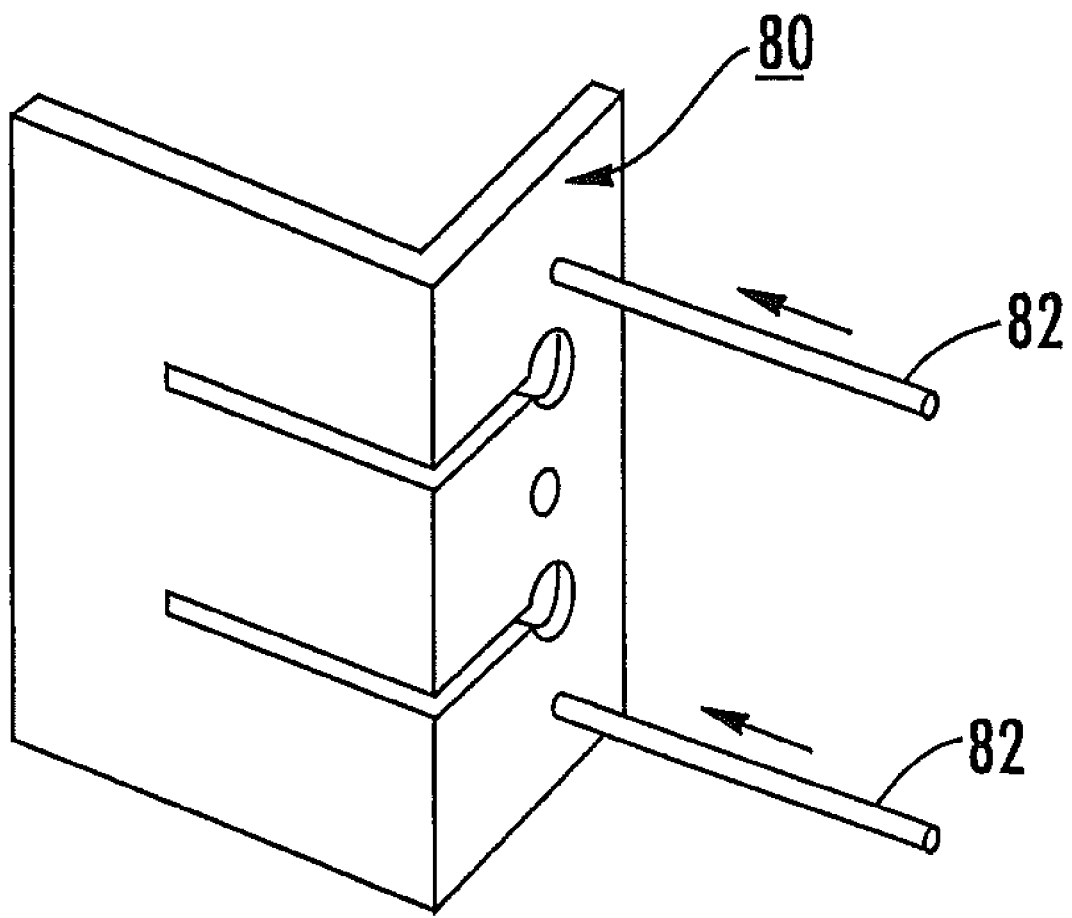
Figure 10:
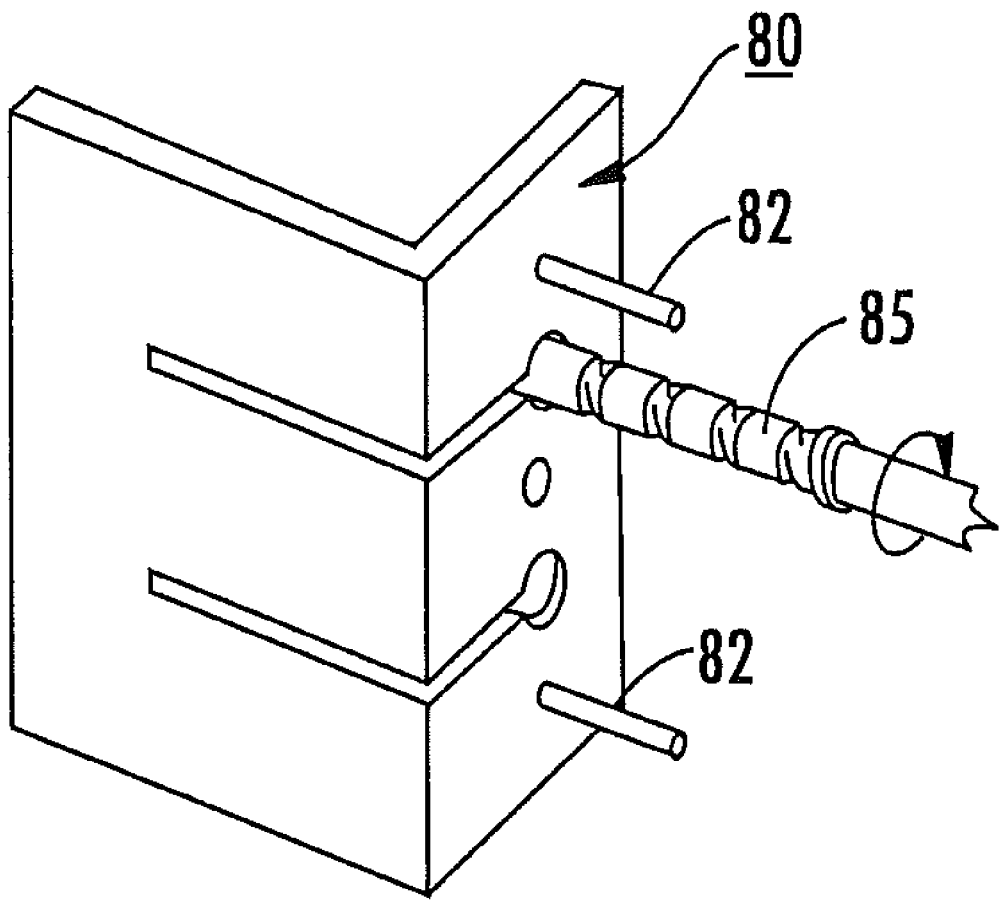
FIG. 10 is a schematic illustration of a drill that extends through the jig shown in FIGS. 9A and 9B to define an anchoring tunnel, aperture or hole for the trapezial implant according to some embodiments of the invention.
Figure 11A:
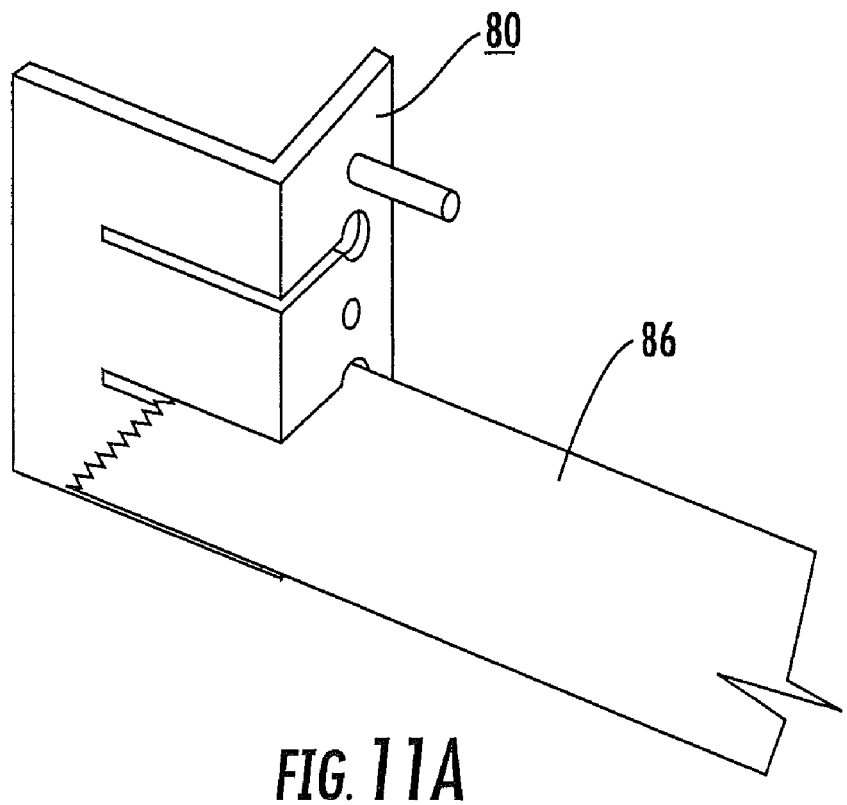
FIG. 11A is a schematic illustration of a saw that extends through the jig shown in FIGS. 9A and 9B to connect the anchoring holes with a distal cut surface of the trapezium according to embodiments of the invention.
Figure 11B:
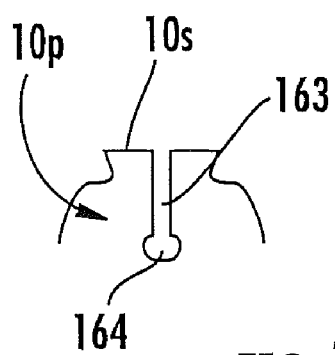
FIG. 11B is a schematic illustration of a surgically prepared trapezium according to embodiments of the invention.

As shown in FIG. 9B, in some embodiments, a plurality of holding members 82, such as 0.35 or 45 kirschner wires, can be used to secure the jig 80 to the trapezium 10. FIG. 10 illustrates a suitably sized drill bit 85 (e.g., a 3/32" drill bit) with a stop feature can be used to drill the lower anchoring holes 164 (FIG. 11B) for the trapezial implant 60. Referring to FIGS. 11A and 11B, a cutting member 86, such as a microsagital saw, can be used to form bone tunnels or channels 163 that connect the anchoring holes 164 with the distal cut surface 10s of the trapezium to four a prepared implant site 10p as shown in FIG. 11B. The cutting may be done with a knife rather than a saw. Also, the cutting may be done before or after the drilling.

Figure 12:
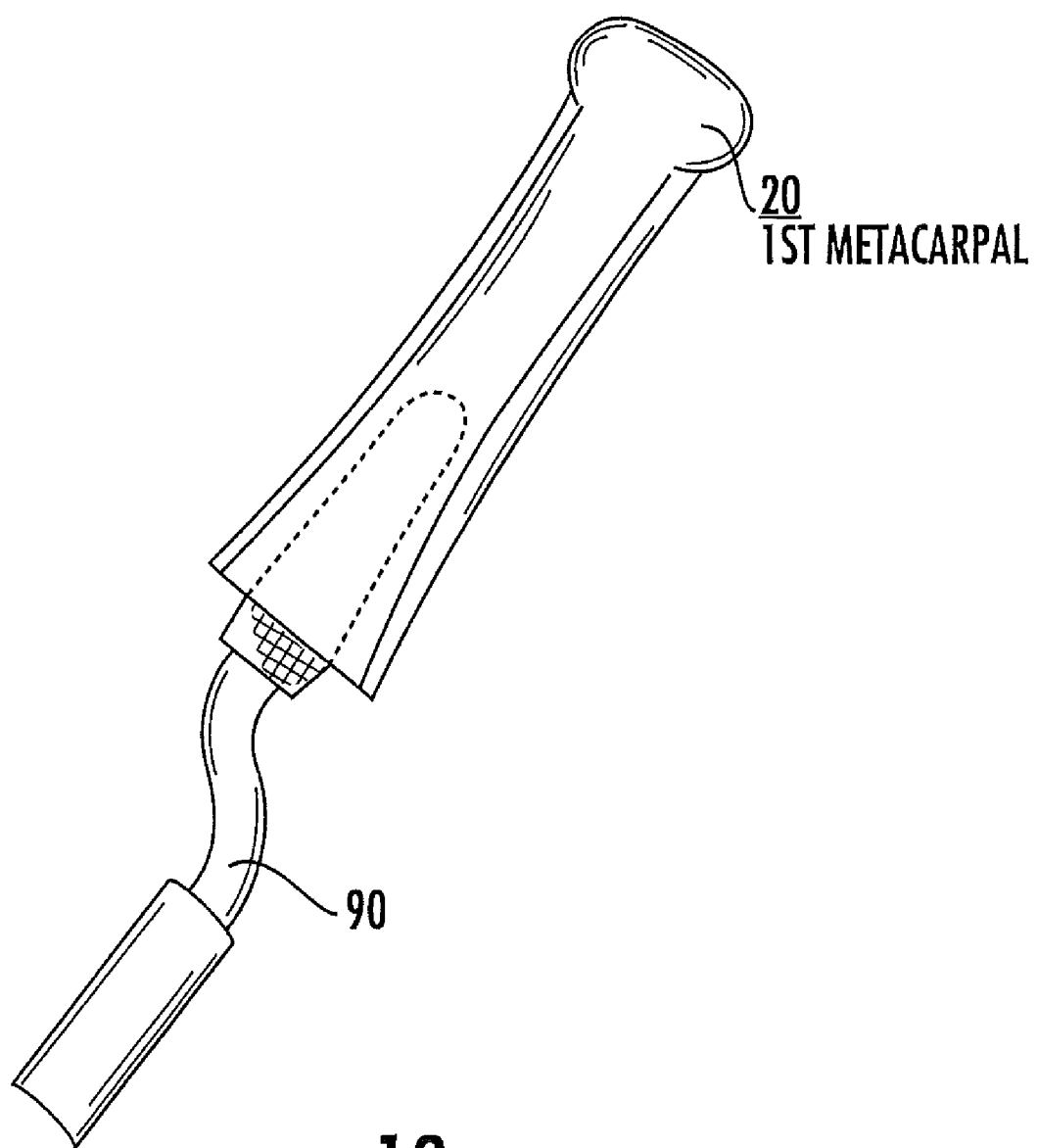
FIG. 12 is a schematic illustration of a broach that can be used to size the 1st metacarpal implant. A trial can be inserted to determine the appropriate implant size.
Figure 13A:
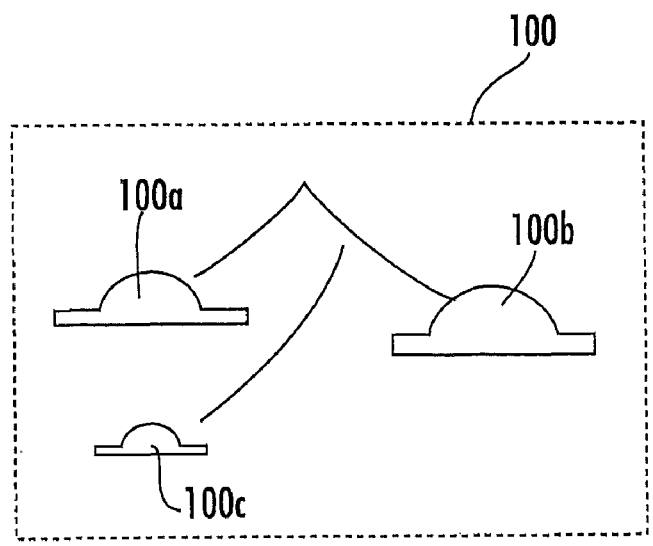
FIG. 13A is a schematic illustration of a medical set or kit of different sized trapezium trials according to embodiments of the present invention.
Figure 13B:
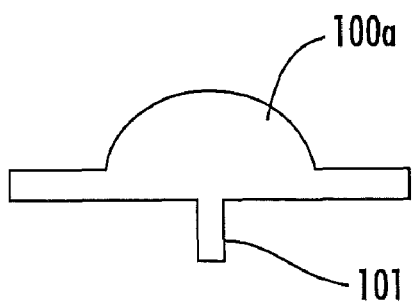
FIGS. 13B and 13C are alternate end views of other trapezium trials according to embodiments of the present invention.
Figure 13C:
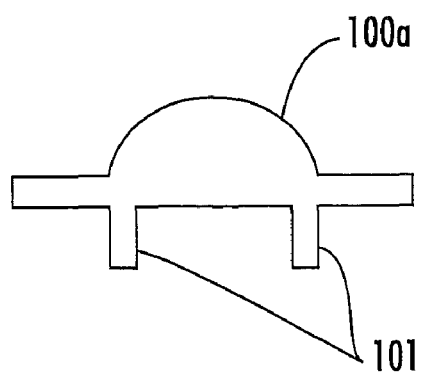

The trapezial jig 80 can be removed and the thumb ray can be extended and adducted to expose the base of the 1$^{st}$ MC for intramedullary sizing. As shown in FIG. 12, broaches 90 can be inserted to size the 1$^{st}$ MC. Intramedullary trials 190 (FIG. 22) can be used to select an intramedullary implant 40 or 42 of the desired size. Trapezial trials 100 can also be inserted to establish a suitable trapezium implant 60 size/configuration. As shown in FIG. 13A, the trapezium trials 100a, 100b, 100c (corresponding to different sizes) can be provided as a kit 100. In FIG. 13A, the trials 100a-c do not include the anchoring member(s) 63. However, as shown in FIGS. 13B and 13C, the trials 100a (only one trial is shown) can include at least one relatively thin fin 101 that can fit into the anchoring member channel and act as a post that can inhibit rotation during the trialing (but do not bind or lock into position). The thumb ray is distracted and the space created is sized. A 1$^{st}$ MC trial 190 (typically without the 1$^{st}$ MC articulating surface) can be attached to the 1$^{st}$ MC intramedullary trial. Range of motion is tested. The final implants 42, 45, 60 can be inserted in the following order: 1$^{st}$ MC intramedullary implant 42, trapezial articulating implant 60, and 1$^{st}$ MC articulating implant 45. Once positioned, the surgeon can proceed with capsular, muscle and skin closure and can optionally reinforce the capsule with a GRAFT JACKET reinforcement (Wright Medical Technologies). A removable thumb spica splint can be used for support and range of motion can begin early.

Figure 14:
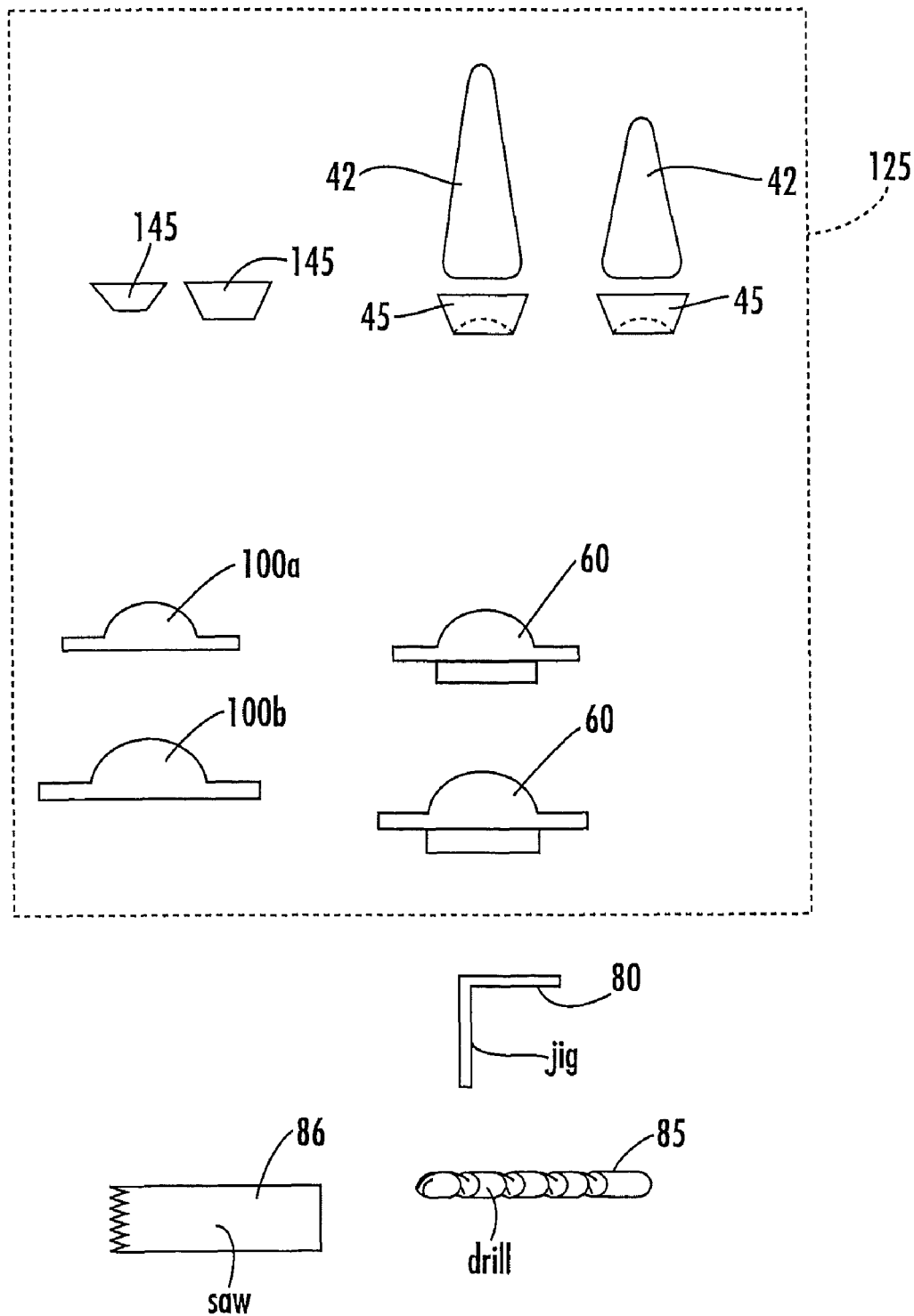
FIG. 14 is a schematic illustration of a medical set or kit of different components for a CMC total joint replacement procedure according to embodiments of the invention.

FIG. 14 illustrates an exemplary medical kit 125 that can include trial base implants 145, trial trapezium implants 100a, 100b, a selection of different size actual implants 42, 45, 60 (or these may be provided separately in individual sterilized sealed packages) and optionally broaches 90 and/or intramedullary trials 190 (not shown), all in a sterile package or packages. The kit 125 may also include the jig(s) 80, saw 86 and/or drill bit 85 (with or without drill).

Figure 15:
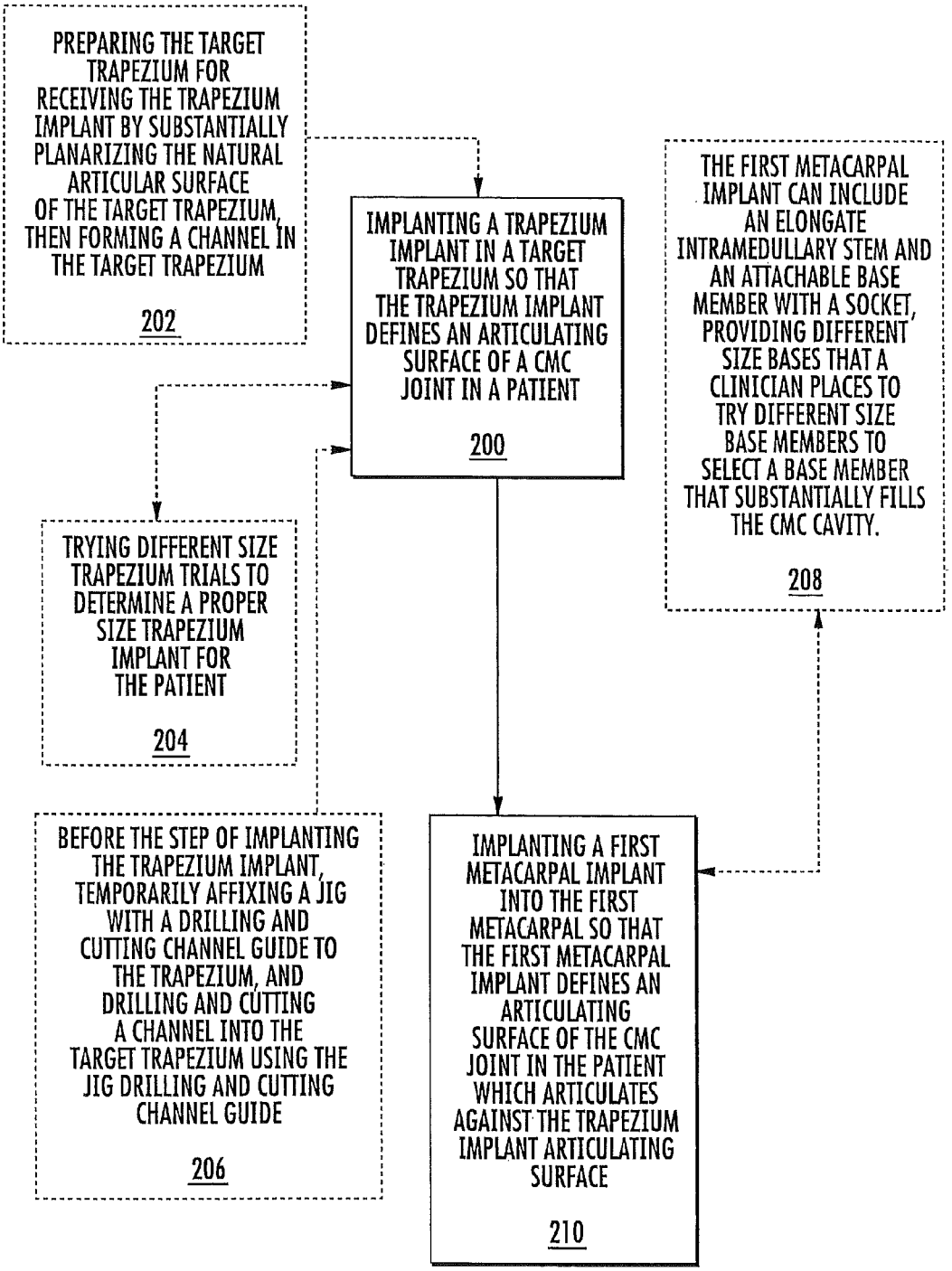
FIG. 15 is a flow chart of exemplary operations that can be used to carry out embodiments of the invention.

FIG. 15 is a flow chart of exemplary operations that can be used to carry out embodiments of the invention. As shown, a trapezium implant can be implanted in a target (prepared) trapezium so that the trapezium defines an articulating surface of a CMC joint in a patient (block 200).

In some particular embodiments, the target trapezium can be prepared for receiving the trapezium implant by planarizing the natural articular surface of the target trapezium (removing a thin wafer), then forming at least one channel in the target trapezium (block 202). Different size trapezium trials can be positioned in the CMC joint to determine a proper size trapezium implant for the patient (block 204).

In some embodiments, before the step of implanting the trapezium implant, a jig with a drilling and cutting channel guide can be temporarily affixed to the trapezium, and at least one channel can be drilled and/or cut into the target trapezium using the jig drilling and cutting channel guide (block 206).

The first metacarpal implant can include an elongate intramedullary stem and an attachable base member with a socket, and before the step of implanting the first metacarpal implant, the method may include trying different size base members to select a base member that substantially fills the CMC cavity (block 208).

Figure 16:
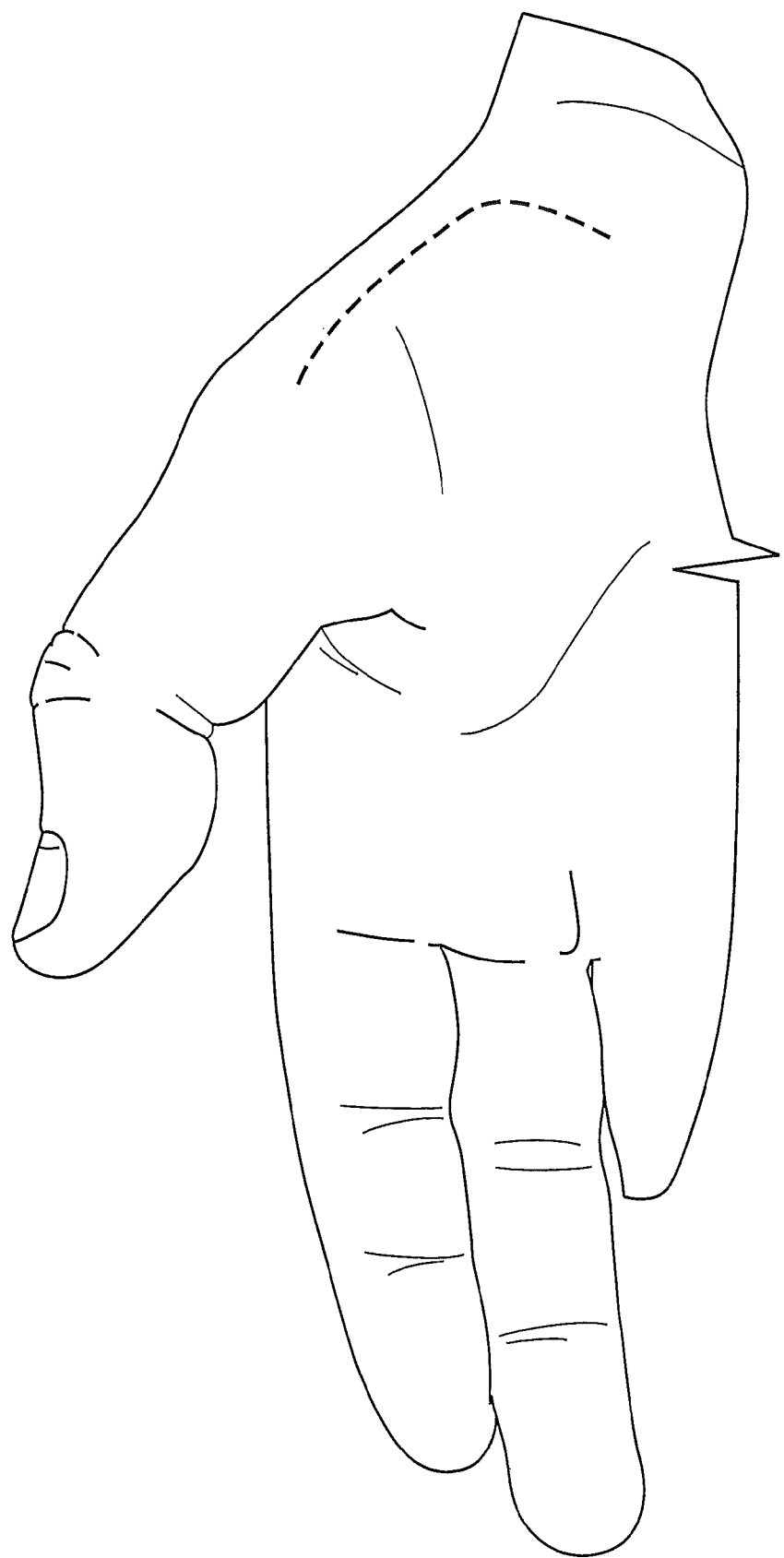
Figure 17:
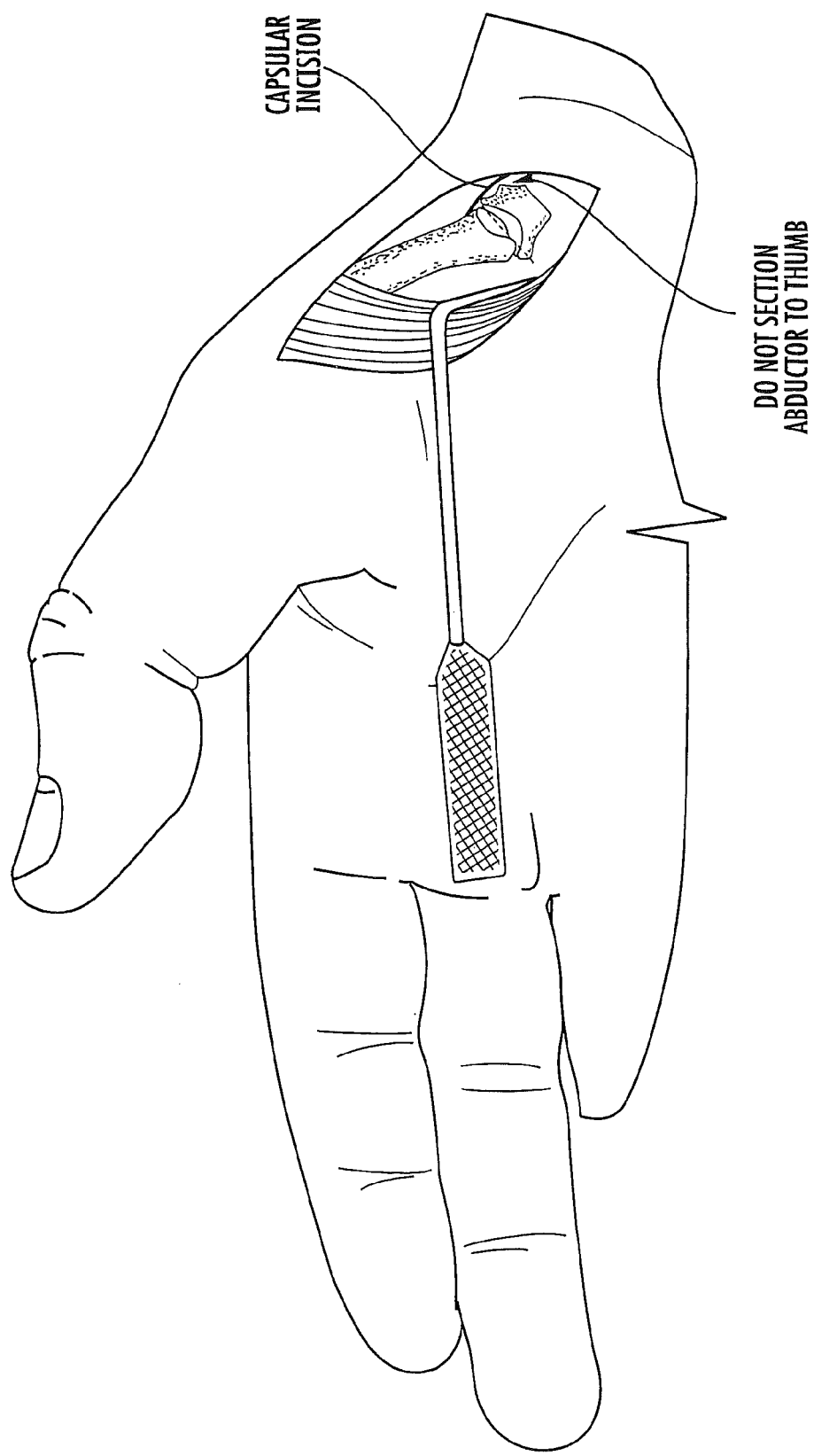
Figure 18:
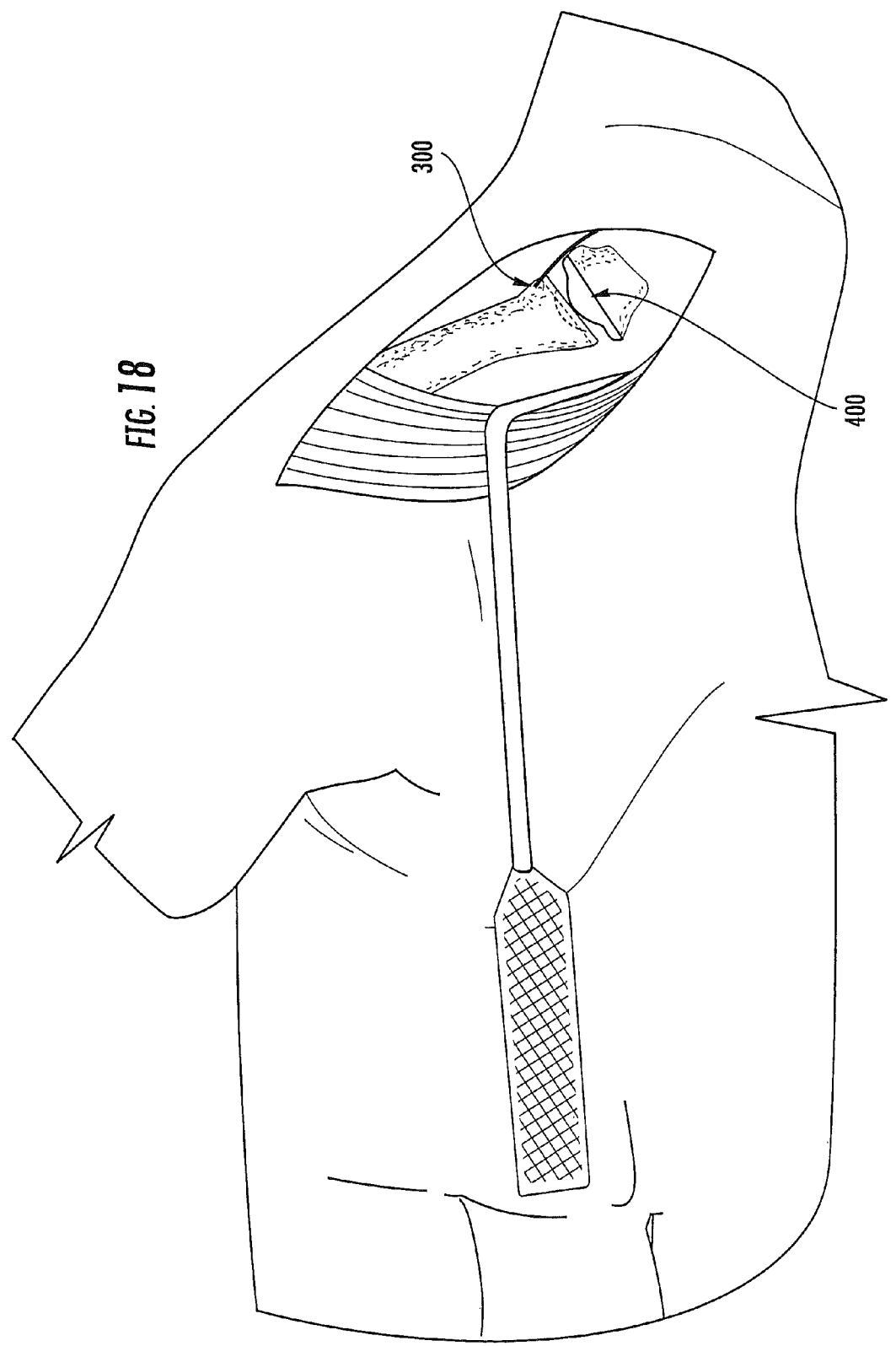
Figure 19:
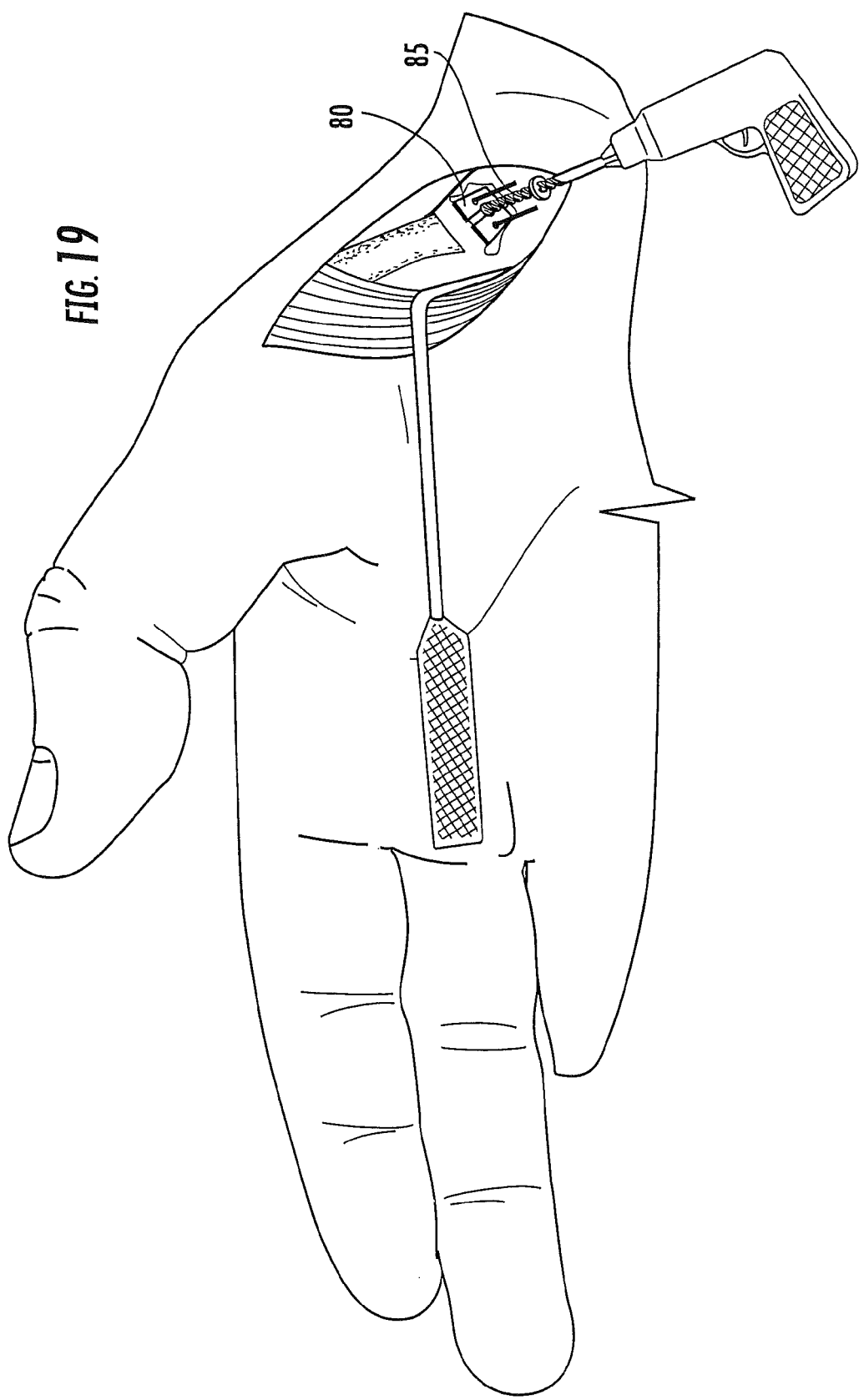
Figure 20:
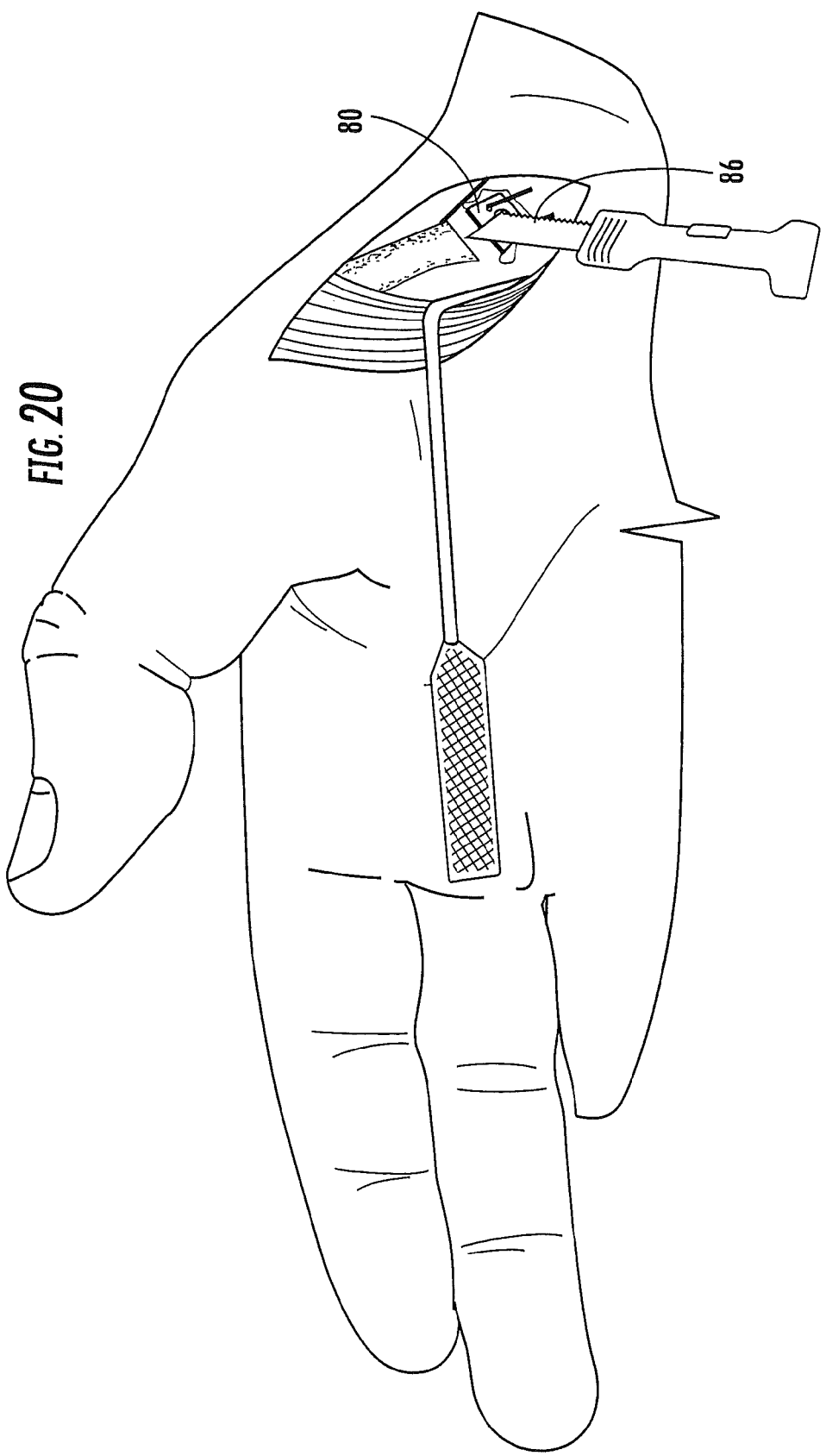
Figure 21:
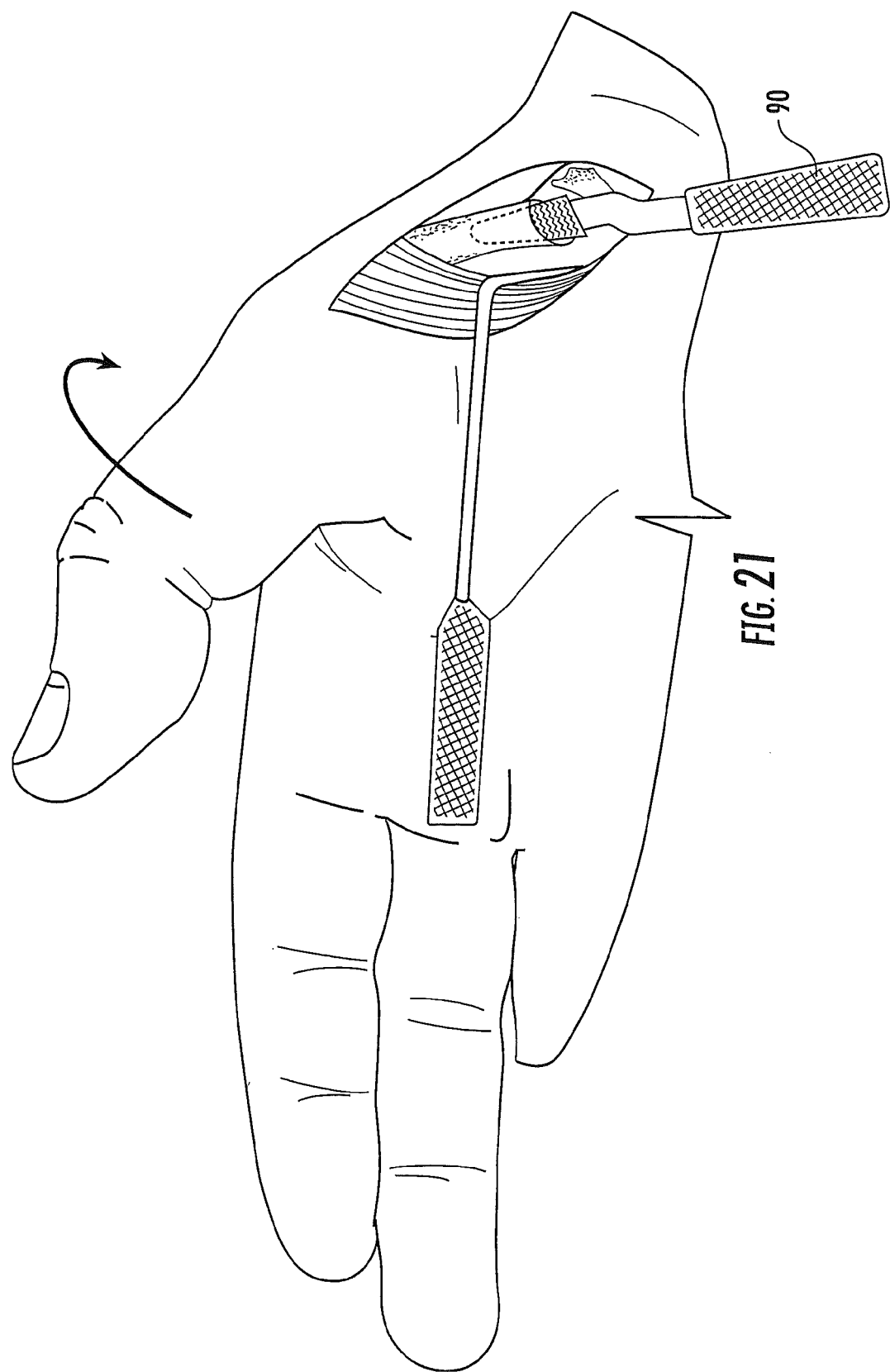
Figure 22:
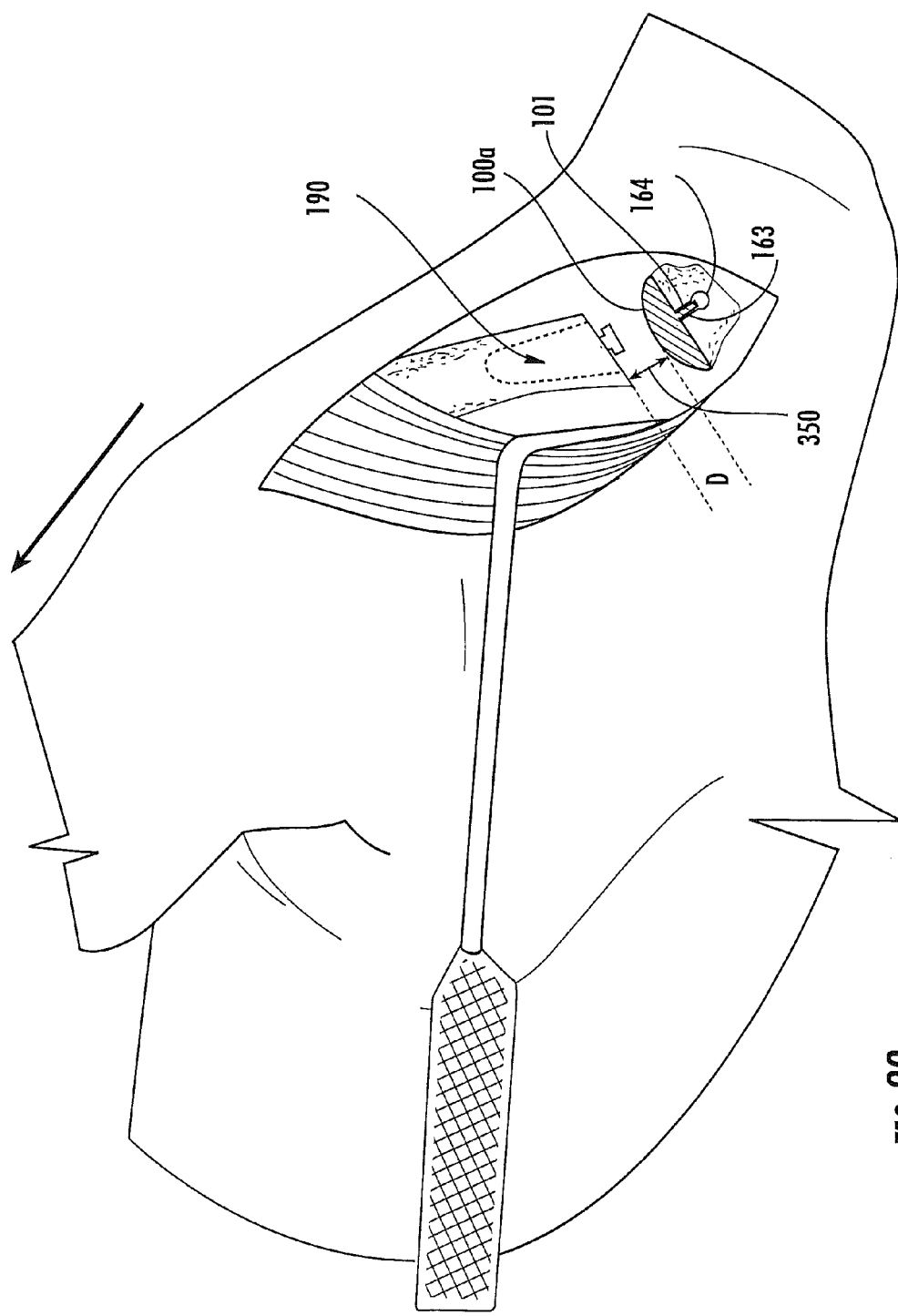

FIGS. 16-23 schematically illustrate the steps in an exemplary surgical procedure. FIG. 16 illustrates that a Wagner incision is made. FIG. 17 illustrates that a capsular incision (do not section abductor to thumb). FIG. 18 illustrates the 1st metacarpal articular resection 300 (variable according to space needed) and a minimal trapezium resection 400 to preserve bone for the trapezium implant 60. FIG. 19 illustrates the jig 80 in position (pinned in place) and a drill 85 used to create the anchoring hole 164 for the keel 63. As shown, the drill bit 85 can include a stop collar to inhibit forward movement of the drill into the trapezium at a certain distance. FIG. 20 illustrates the saw 86 for creating the keel shaft 163 in the bone. FIG. 21 shows the thumb adducted and extended for the first metacarpal base exposure and a broach 93 used to (rasp, broach and/or prepare) an intramedullary space for the first metacarpal implant 40. FIG. 22 illustrates the placement of the trapezium trial 100a (with anti-rotational fin 101) and first metacarpal trial 190. A clinician can measure or size the distance or size "D" of the gap 350 created between the first metacarpal base and the trapezial implant 60, then select the appropriate articulating thickness. As shown, where a separate base member 45 is used, this member 45 can define the articulating thickness. In other embodiments, the entire implant 40 can be selected from a kit to provide the desired thickness.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A medical kit for thumb CMC joint arthroplasty, comprising:
   at least one thumb trapezium implant, wherein the at least one thumb trapezium implant comprises at least one downwardly extending anchoring member having a planar first portion with a constant thickness extending in a depth direction, the planar first portion having a perimeter with parallel straight short sides that merges into a lower second portion of the at least one anchoring member, the lower second portion having a substantially circular cross-sectional shape, wherein a cross-sectional size of the substantially circular shape is greater than a thickness of the planar first portion, and wherein the at least one anchoring member is configured to slidably enter a slot in a target trapezium having a corresponding shape as the at least one anchoring member from a radial surgical approach;
   at least one thumb first metacarpal intramedullary stem implant, wherein, in position, the thumb first metacarpal intramedullary implant and the trapezium implant articulate against each other; and
   at least one trapezium implant jig with at least one downwardly extending flat slot with parallel straight sides configured to define a bone preparation guide or template for preparing at least one slot in a target trapezium from a volar radial surgical approach, the slot sized and configured to slidably snugly accept the trapezium implant anchoring member from the volar radial surgical approach, wherein the trapezium implant jig comprises a plurality of substantially aligned spaced apart fixation apertures for accepting members to secure the jig in position during formation of the slot in the target trapezium, and wherein the jig comprises a substantially "L" shaped body with a top portion that merges into a downwardly extending side portion, with the side portion being substantially orthogonal to the top portion and having a shorter length, wherein the jig at least one downwardly extending slot is configured to continuously extend from the downwardly extending portion upward and across the top portion to define a substantially horizontal slot extending through a top surface of the jig, and wherein the at least one jig slot has a circular aperture on a lower end of the side portion.

2. The medical kit of claim 1, wherein the trapezium implant and the first metacarpal implant have articulating surfaces with contours similar to natural articular surfaces of a CMC joint.

3. The medical kit of claim 1, wherein the jig downwardly extending at least one slot is two spaced apart parallel slots, and wherein the spaced apart fixation apertures include one fixation aperture on each outer side of a respective slot and one between the two slots, each fixation aperture being substantially aligned with the circular aperture of the slots.

4. The medical kit of claim 1, wherein the at least one anchoring member is configured to be resistance fit into a corresponding slot in the target trapezium.

5. The medical kit of claim 1, further comprising a plurality of trapezium implant trials, wherein the trials have a substantially planar bottom surface devoid of any downwardly projecting anchoring member or the trials have at least one downwardly extending anti-rotational post.

6. The medical kit of claim 1, further comprising a plurality of trapezium implant trials, wherein the trials have one downwardly extending substantially planar anti-rotational post.

7. The medical kit of claim 1, further comprising a plurality of trapezium implant trials, wherein the trials have a planar fin with a length that is shorter than that of the anchoring member of the trapezium implant.

* * * * *